(12) United States Patent
Leren et al.

(10) Patent No.: US 9,133,256 B2
(45) Date of Patent: Sep. 15, 2015

(54) HATCHING FLUID ENZYMES AND USES THEREOF

(75) Inventors: Hans Kristian Leren, Bergen (NO); Bernt Th. Walther, Bergen (NO)

(73) Assignee: AQUA BIO TECHNOLOGY ASA, Bergen (NO)

( * ) Notice: Subject to any disclaimer, the term of this patent is extended or adjusted under 35 U.S.C. 154(b) by 0 days.

(21) Appl. No.: 13/511,326

(22) PCT Filed: Nov. 30, 2010

(86) PCT No.: PCT/EP2010/068509
§ 371 (c)(1),
(2), (4) Date: Aug. 8, 2012

(87) PCT Pub. No.: WO2011/064384
PCT Pub. Date: Jun. 3, 2011

(65) Prior Publication Data
US 2012/0309689 A1 Dec. 6, 2012

(30) Foreign Application Priority Data

Nov. 30, 2009 (GB) .................................. 0921001.4

(51) Int. Cl.
| | | |
|---|---|---|
| *A61K 8/64* | (2006.01) | |
| *A61K 8/66* | (2006.01) | |
| *A61Q 19/00* | (2006.01) | |
| *C07K 14/46* | (2006.01) | |
| *C12N 9/64* | (2006.01) | |
| *A61K 8/60* | (2006.01) | |
| *A61Q 19/02* | (2006.01) | |
| *A61Q 19/10* | (2006.01) | |

(52) U.S. Cl.
CPC ............... *C07K 14/461* (2013.01); *A61K 8/606* (2013.01); *A61K 8/64* (2013.01); *A61Q 19/00* (2013.01); *A61Q 19/02* (2013.01); *A61Q 19/10* (2013.01); *C12N 9/6402* (2013.01); *A61K 2800/28* (2013.01)

(58) Field of Classification Search
None
See application file for complete search history.

(56) References Cited

U.S. PATENT DOCUMENTS

| | | | |
|---|---|---|---|
| 5,961,981 | A | 10/1999 | Gutierrez |
| 2004/0101580 | A1 | 5/2004 | Msika et al. |
| 2009/0117093 | A1 | 5/2009 | Kim |
| 2009/0214512 | A1 | 8/2009 | Miyazaki et al. |

FOREIGN PATENT DOCUMENTS

| | | |
|---|---|---|
| JP | 2001-354582 | 12/2001 |
| JP | 2006-516888 | 7/2006 |
| WO | 97/25998 | 7/1997 |
| WO | 99/29836 | 6/1999 |
| WO | 02/066624 | 8/2002 |
| WO | WO 02066624 A2 * | 8/2002 |
| WO | 2004/056983 | 7/2004 |
| WO | 2005/046709 | 5/2005 |

OTHER PUBLICATIONS

UniProtKB/TrEMBL Accession No. C1KG91, entry date of May 26, 2009, accessed May 15, 2014 at URL uniprot.org/uniprot/C1KG91.*
GenBank Accession No. FJ824909, entry date of Apr. 12, 2009 (accessed May 20, 2014 at URL ncbi.nlm.nih.gov/nuccore/FJ824909).*
Oppen-Berntsen D. et al., Salmon Eggshell Protein Expression: A Marker for Environmental Estrogens, Marine Biotechnology, May 1999, vol. 1, pp. 252-260.
Database EMBL [Online], Apr. 13, 2009, Salmo salar hatching enzyme mRNA, complete cds., retrieved from EBI accession No. EMBL: FJ824909.
Yasumasu, S. et al., Isolation and Some Properties of Low Choriolytic Enzyme (LCE), a Component of the Hatching Enzyme of the Teleost, *Oryzias latipes*, J. Biochem.,105, pp. 212-218 (1989).
New Zealand Further Examination Report, dated Nov. 5, 2014, for New Zealand Patent Application No. 627941.
Russian Office Action, dated Sep. 30, 2014, for Russian Patent Application No. 2012127298, and English translation thereof.
Japanese Office Action, dated Nov. 27, 2014, for Japanese Patent Application No. 2012-540460, and English translation thereof.
GenBank Accession No. AAD56572.1, published Sep. 12, 2001.
GenBank Accession No. DT135177.1, published Aug. 15, 2005.
GenBank Accession No. BJ905112, published Dec. 18, 2010.
GenBank Accession No. AJ000665.1, published Nov. 14, 2006.
GenBank Accession No. ABW17264.1, published Feb. 8, 2008.
GenBank Accession No. ABW17265.1, published Feb. 8, 2008.
GenBank Accession No. BAG06176.1, published May 22, 2008.
Chilean Examination Report, dated Jun. 5, 2015, for Chilean Patent Application No. 1380-2012.

* cited by examiner

*Primary Examiner* — Julie Ha
*Assistant Examiner* — Kristina M Hellman
(74) *Attorney, Agent, or Firm* — Roylance, Abrams, Berdo & Goodman, L.L.P.

(57) ABSTRACT

The present invention relates to various polypeptides from fish hatching fluid, their encoding nucleic acid sequences, pharmaceutical compositions comprising said polypeptides and nucleic acid molecules and their use in various medical and cosmetic applications to the skin, particularly for moisturizing skin and/or for exfoliation of the horny layer of the skin for treating or preventing skin disorders or conditions in an animal.

17 Claims, 6 Drawing Sheets

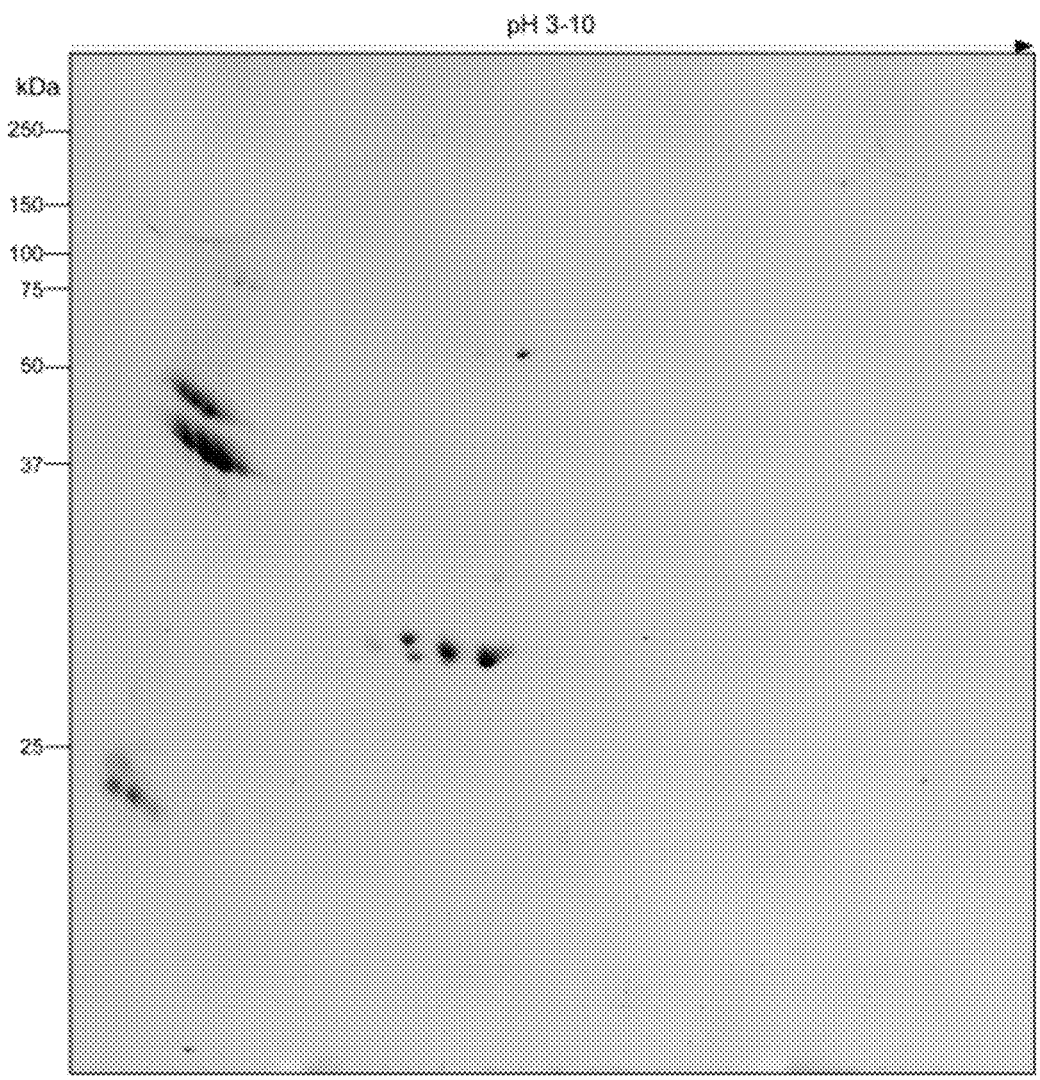

HATCHING FLUID ENZYMES AND USES THEREOF

The present invention relates to the use of choriolysin and very acidic proteins (VAPs) derivable from fish hatching fluid, alone or in combination in various cosmetic and medical applications to the skin. The present invention also relates to the very acidic proteins which are described for these uses.

The skin is one of the more vulnerable organs of the body. Though seldom life-threatening, skin disorders or conditions can be uncomfortable and may cause chronic disabilities. In addition, because the skin is so visible, skin disorders and conditions can lead to psychological stress. There is therefore a continuing need for effective treatments of skin conditions and disorders.

Skin forms the largest organ of the body, accounting for about 12-16 percent of a person's weight. It performs many vital roles as both a barrier and a regulating influence between the outside world and the controlled environment within our bodies.

Skin consists of 3 layers, namely the epidermis, dermis and subcutis. The epidermis is the uppermost, epithelial layer of the skin. It acts as a physical barrier, preventing loss of water from the body, and preventing entry of substances and organisms into the body. Its thickness varies according to body site.

The epidermis consists of stratified squamous epithelium, i.e. it consists of layers of flattened cells. Skin, hair and nails are keratinised, meaning they have a dead, hardened hydrophobic surface made of a protein called keratin. Epidermis is made impermeable due to its contents of extracellular lipids associated with keratinocytes, especially in the middle layer of the epidermis (stratum lucidum). Mucous membranes (e.g. of the oesophagus, oral pharyngeal cavity, reproductive organs, and others) are mainly non-keratinised and moist. The epidermis has three main types of cell, namely keratinocytes (skin cells), melanocytes (pigment-producing cells) and Langerhans cells (immune cells). The Merkel cell is a fourth, less prevalent, epidermal cell.

The keratinocytes mature and differentiate with accumulation of keratin as they move outwards. They eventually fall or rub off. They form four or five distinct strata, which from the most superficial to the deepest are (i) the Stratum corneum (horny layer) with dead, dried-out hard cells without nuclei, (ii) the Stratum granulosum (granular layer) with cells containing basophilic granules and outwardly separated from stratum corneum by the thin stratum lucidum, (iii) the Stratum spinulosum (spinous, spiny or prickle cell layer) in which the cells become increasingly flattened as they move upward and (iv) the Stratum basale (basal layer) with columnar (tall) regenerative cells.

Immediately below the epidermis is the basement membrane, a specialised structure that lies between the epidermis and dermis.

The dermis is the fibrous connective tissue or supportive layer of the skin. The major fibres are collagen fibres and elastin which are interwoven.

The subcutis is the fat layer immediately below the dermis and epidermis. It is also called subcutaneous tissue, hypodermis or panniculus. The subcutis mainly consists of fat cells (adipocytes), nerves and blood vessels.

New epithelial skin cells are created in the skin's lower layer, the stratum granulosum. Over time, cells migrate to the surface of the skin and become more acidic. During their 30 day journey, they die and become saturated with keratin. Keratin and associated lipids are important because they protect the skin from outside elements.

Disease, injury, environmental factors, age, hormone levels, medication, externally applied or ingested materials, genetic conditions or a variety of other factors may lead to abnormal functioning of the skin resulting in irregularities or abnormalities. Some of these irregularities or abnormalities may be purely cosmetic in nature, e.g. dry skin, wrinkles or altered pigmentation, or may be more severe leading to pain or discomfort, e.g. eczema and psoriasis.

Dry skin is one of the most common skin conditions or abnormalities. Although certain individuals are more susceptible to dry skin, the condition can affect anyone, regardless of age, gender, or skin type.

Dry skin occurs when the skin's outer layer (the stratum corneum with the stratum lucidum) is depleted of water. When this layer is well-moistened, it minimizes water loss through the skin and helps keep out irritants, allergens, and germs. However, when the stratum corneum dries out, its protective function is reduced. This allows greater water loss, leaving skin vulnerable to environmental factors.

Under normal conditions, the stratum corneum has a water content of 10% to 30%. This water imparts to the skin its soft, smooth, and flexible texture. The water comes from the atmosphere, the underlying layers of skin, and sweat. Oil produced by skin glands and fatty substances produced by skin cells act as natural moisturizers, allowing the stratum corneum to seal in water.

The body continuously loses water from the skin's surface by evaporation. Under normal conditions, the rate of loss is slow, and the water is adequately replaced. Characteristic signs and symptoms of dry skin occur when the water loss exceeds the water replacement, and the stratum corneum's water content falls below 10%.

Moisturizers which improve or eradicate dry skin are highly desirable. Whilst many moisturizers are known in the art, there remains a need for natural products which are effective yet gentle.

Another common skin abnormality or condition is excessive amounts of the horny layer of the skin. This may result from failure of the horny layer to be sloughed off or through excessive keratin deposition in the horny layer. The former may result when the natural process of skin erosion becomes uneven, which gives skin a dry and rough character. Benign hyperproliferative disorders include epidermolytic hyperkeratosis (or cracked skin) and hair follicle keratosis. One common benign hyperproliferative condition is peripheral hypertrophy around scars and/or formation of keloids. Other hyperproliferative conditions are corns, calluses, hyperkeratotic warts (particularly veruca vulgaris), ichthyoses and palmoplantar keratoses.

Current treatments involve exfoliation or surgery in extreme cases. Hyperkeratosis is usually treated by softening the horny layer and removing the thickened skin.

Exfoliation may also be used to remove impaired epidermal cells, e.g. epidermal cells from an epidermis exhibiting a pigmentation disorder, e.g. liver spots.

Exfoliation removes the outer strata of epidermis to reveal the newer skin cells beneath. Exfoliation may be achieved by physical means (i.e. abrasion of the skin) or by chemical means. Chemical exfoliants include scrubs containing salicylic acid, glycolic acid, fruit enzymes, citric acid or malic acid and may be applied in high concentrations by a dermatologist, or in lower concentrations in over-the-counter products. Chemical exfoliation may involve the use of products that contain alpha hydroxy acids (AHAs) or beta hydroxy acids (BHAs), or enzymes that act to loosen the glue-like substances that hold the cells together at cell junctions, allowing them to ease away. This type of exfoliation is recommended for people treating acne.

The greatest disadvantage to exfoliation is the high price of some of the products and methods used to achieve it. Exfoliation will lead to some initial redness to the skin. Near the end of chemical peels, the skin will frost, with colours varying from a bright white to gray on the skin surface. More effective methods which are gentler on the skin are therefore desirable.

There thus remains a need for treatments suitable for moisturizing skin and/or for exfoliation of the horny layer of the skin.

Certain molecules which are found in fish hatching fluid have surprisingly now been found to be remarkably effective moisturizers and exfoliants, namely choriolysin and a newly identified group of very acidic proteins (VAPs).

Hatching of fish embryos is achieved, at least in part, by the so-called hatching enzymes, choriolysins. Choriolysin is a metalloproteinase found in fish hatching fluid and is generally found in two forms, namely the high choriolytic enzyme (choriolysin H, HCE) and the low choriolytic enzyme (choriolysin L, LCE), which are similar in some structural and catalytic characteristics and belong to the astacin family but with markedly different substrate preferences.

In salmon the LCE is relatively unusual compared to known choriolysins from other fish species and may be applied for purposes which are described hereinafter. The sequence of salmon LCE is set forth in SEQ ID No. 1, below.

As mentioned above, a group of very acidic proteins (VAPs) have now been identified in fish hatching fluid by precipitation from other components in 80% acetone and removal of the acetone by evaporation of the centrifuged pellet as described in the Examples.

These VAPs are generated by proteolytic cleavage of the polymerized and cross-linked eggshell or chorion by hatching enzymes during hatching and are fragments of components incorporated into the chorion during oogenesis, such as choriogenin H and L as described hereinbelow in more detail. These fragments of choriogenic proteins, which here are termed VAPs, are released into the perivitelline fluid during hatching to become components of the hatching fluid. VAPs appear in various forms. When analyzed by isoelectric focussing (see the Examples), VAPs I, II and III (as discussed below) appear in at least 2, 6 and 3 isoforms, respectively.

We disclose herein three VAPs which have been identified and which have surprising properties as described hereinafter. The sequences of these VAPs have been determined by mass spectroscopy as described in the Examples and are presented in SEQ ID Nos. 2-4.

VAPs I, II and III as referred to herein have the sequences as set forth in SEQ ID Nos. 2, 3 and 4, respectively.

VAP I is 117 amino acids in size and has a molecular weight of around 15.5 kDa and pl around 3.5. This VAP is a fragment of a 439 amino acid, 57 kDa eggshell protein (also referred to as zona radiata protein, SEQ ID No. 5). VAP I may alternatively be derived from a homologous zona radiata protein comprising 467 amino acid residues (SEQ ID NO: 8).

VAP II is 261 amino acids in size and has a molecular weight of around 35 kDa and pl around 4.0. This VAP is a fragment of a 524 amino acid protein, 68 kDa choriogenin H beta (SEQ ID No. 6).

VAP III is 224 amino acids in size and has a molecular weight of around 29 kDa and pl around 5.2. This VAP is a fragment of a 438 amino acid protein, 57 kDa choriogenin L (SEQ ID No. 7).

As shown in the Examples and discussed above, each VAP may exist in various isoforms.

Thus, in a first aspect the present invention provides a polypeptide consisting of:
(i) an amino acid sequence as set forth in any one of SEQ ID Nos. 2-4 or a sequence which is at least 50% identical to said sequence, or a portion of any of said sequences; and optionally
(ii) a flanking amino acid sequence at the N and/or C terminal of the amino acid sequence in (i) which is from 1 to 100 amino acids in length.

"Polypeptides" as referred to herein are molecules with preferably more than 50, 100, 150, 200 or 250 residues and/or less than 400, 300, 200 or 100 residues or a range selected therefrom. As referred to herein a "portion" preferably comprises at least 30, 40, 50, 60, 70, 80, 90, 100, 150, 200 or more amino acids of the sequence from which it is derived. Said portion may be obtained from a central or N-terminal or C-terminal portion of the sequence. In a preferred aspect said portion consists of the full length sequence from which it is derived from which at least 1, 2, 3, 4 or 5 amino acid residues have been removed, preferably from the N-terminus.

As referred to herein a "flanking sequence" is an amino acid sequence which is attached at the terminal N or C end of the central amino acid sequence via normal peptide bonds to form a continuous amino acid sequence (except as modified in functional equivalents as discussed hereinbelow). A flanking sequence may be present on the N or C terminal end of the central amino acid sequence or may be present on both ends. The flanking sequence may be as short as 1 amino acid or as long as 100 amino acids, preferably from 1-50 (or from 5-100 or 10-50), e.g. 1-25, e.g. 1-5 amino acids in length. When flanking sequences are present at both the N and C terminal ends they may be of the same or different sequences and may be of the same or different lengths. The flanking sequences may be derived from the native sequence of which the VAP in question is a fragment or may have less than 80, 70, 60 or 50% identity to the native sequence in the comparable portion (see e.g. native sequences relative to SEQ ID Nos. 2-4 provided in SEQ ID Nos. 5-7, respectively and SEQ ID No: 8, which provides an alternative native sequence for SEQ ID No. 2).

Preferably said sequence in part (i) above is at least 55, 60, 65, 70, 75, 80, 85, 90, 95, 96, 97, 98 or 99% identical to the sequence (SEQ ID Nos 2-8) to which it is compared.

Sequence identity may be determined by, e.g. using the SWISS-PROT protein sequence databank using FASTA pepcmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100 or 50 contiguous amino acids.

Preferably such sequence identity related polypeptides are functionally equivalent to the polypeptides which are set forth in the recited SEQ ID Nos. Such functionally equivalent polypeptides may take the form of derivatives as set forth below. Similarly, the polypeptides with sequences as set forth in the SEQ ID Nos. may be modified without affecting the sequence of the polypeptide as described below.

Furthermore, "portions" as described herein may be functionally equivalents. Preferably these portions satisfy the identity (relative to a comparable region) conditions mentioned herein. Preferred polypeptides of the invention including portions and polypeptides which include the above described flanking sequences are preferably acidic, e.g. have a pl from 3 to 5.5, preferably from 3.5 to 5.2.

As referred to herein, to achieve "functional equivalence" the polypeptide may show some reduced efficacy in performing the medical or cosmetic function relative to the parent molecule (i.e. the molecule from which it was derived, e.g. by amino acid substitution), but preferably is as efficient or is more efficient. Thus, functional equivalence relates to a polypeptide which is effective to treat a condition or disorder or to cosmetically improve the condition and/or appearance of skin as referred to herein, i.e. to reduce one or more symptoms of the patient, e.g. the appearance, texture, thickness or moisture content of the skin as described hereinafter. This may be tested by comparison of the effects of the derivative polypeptide relative to the polypeptide from which it is derived in a qualitative or quantitative manner, e.g. by performing the analyses referred to in the Examples. Where quantitative results are possible, the derivative is at least 30, 50, 70 or 90% as effective as the parent polypeptide.

Functionally-equivalent proteins which are related to or derived from the naturally-occurring protein, may be obtained by modifying the native amino acid sequence by single or multiple (e.g. 2-20, preferably 2-10) amino acid substitutions, additions and/or deletions (providing they satisfy the above-mentioned sequence identity requirements), but without destroying the molecule's function. Such proteins are encoded by "functionally-equivalent nucleic acid molecules" which are generated by appropriate substitution, addition and/or deletion of one or more bases.

Preferred functional equivalents are "addition" variants in which amino and/or carboxy terminal fusion proteins or polypeptides are generated, comprising an additional protein or polypeptide fused to the parent polypeptide. As described above, any sequences which when added to the central polypeptide form a contiguous amino acid sequence are limited to flanking sequences as described above.

Further preferred functional equivalents are "deletion" or "truncation" variants in which proteins or polypeptides are generated wherein amino and/or carboxy terminal residues have been removed from the central polypeptide. In a particularly preferred embodiment, residues are removed from the amino terminus, wherein at least 1, 2, 3, 4 or 5 amino acid residues are removed. Such functional equivalents are portions as described hereinbefore.

Particularly preferred functionally-equivalent variants are natural biological variations (e.g. allelic variants or geographical variations within a species or alternatively in different genera, e.g. plants, animals or bacteria, particularly fish, particularly from the family Salmonidae, especially the sub-families Salmo and Oncorhynchus) and derivatives prepared using known techniques. For example, nucleic acid molecules encoding functionally-equivalent proteins may be produced by chemical synthesis or in recombinant form using the known techniques of site-directed mutagenesis including deletion, random mutagenesis, or enzymatic cleavage and/or ligation of nucleic acids.

The present invention also provides a nucleic acid molecule consisting of a nucleotide sequence which encodes only said polypeptide or a complementary sequence thereof.

In a preferred aspect, the present invention thus provides a nucleic acid molecule consisting of:
(i) a nucleotide sequence as set forth in any one of SEQ ID Nos. 10-12, a sequence which is at least 50% identical to said sequence, or a sequence which hybridizes to said sequence under non-stringent binding conditions of 6×SSC/50% formamide at room temperature and washing under conditions of high stringency, e.g. 2×SSC, 65° C., where SSC=0.15 M NaCl, 0.015M sodium citrate, pH 7.2, or a sequence complementary to any of the aforesaid sequences, or a portion thereof; and optionally (ii) a flanking nucleotide sequence at the 5' or 3' end of the nucleotide sequence in (i) which is from 1 to 300 nucleotides in length,
or a complementary sequence thereof.

Preferably said nucleic acid molecule encodes a polypeptide as set forth hereinbefore.

"Nucleic acid molecules" as referred to herein are molecules with preferably more than 150, 300, 450, 600 or 750 bases and/or less than 1200, 900, 600 or 300 bases or a range selected therefrom. "Portions" as referred to above, preferably comprise at least 90, 120, 150, 180, 210, 240, 270, 300, 450 or 600 nucleotide bases of the sequence from which it is derived. Preferably said portions encode N-terminal, central or C-terminal peptides as described hereinbefore. In a preferred aspect said portion consists of the full length sequence from which it is derived from which at least 1, 2, 3, 4, 5, 6, 7, 8, 9, 10, 11, 12, 13, 14 or 15 bases have been removed, preferably from the 5' end.

As referred to herein a "flanking sequence" is a nucleotide sequence which is attached at the terminal 5' or 3' end of the central nucleotide sequence via normal phosphodiester bonds to form a continuous nucleotide sequence (except as modified in functional equivalents as discussed hereinbelow). A flanking sequence may be present on the 5' or 3' terminal end of the central nucleotide sequence or may be present on both ends. The flanking sequence may be as short as 1 nucleotide or as long as 300 nucleotides, preferably from 1-150 (or from 15-300 or 30-150), e.g. 1-75, e.g. 1-15 nucleotides in length. When flanking sequences are present at both the 5' and 3' terminal ends they may be of the same or different sequences and may be of the same or different lengths. The flanking sequences may be derived from the native sequence of which the VAP encoding sequence in question is a fragment or may have less than 80, 70, 60 or 50% identity to the native encoding sequence in the comparable portion (see e.g. native sequences relative to SEQ ID Nos. 10-12 provided in SEQ ID Nos 13-15, respectively and SEQ ID No: 16, which provides an alternative native sequence for SEQ ID No. 10).

Preferably said sequence in part (i) above is at least 55, 60, 65, 70, 75, 80, 85, 90, 95, 96, 97, 98 or 99% identical to the sequence (SEQ ID Nos 10-16) to which it is compared.

Sequence identity may be determined by, e.g. FASTA Search using GCG packages, with default values and a variable pamfactor, and gap creation penalty set at 12.0 and gap extension penalty set at 4.0 with a window of 6 nucleotides.

Preferably such sequence identity related or hybridizing nucleic acid molecules are functionally equivalent to the nucleic acid molecules which are set forth in the recited SEQ ID Nos. Such functionally equivalent nucleic acid molecules may take the form of derivatives as set forth below and are considered functionally equivalent if they encode polypeptides which would be considered functional equivalents according to the tests described hereinbefore. Preferred functional equivalents are those which encode the preferred polypeptides as set out above, e.g. nucleic acid molecules which encode polypeptides found in different genera or species than the specific molecules mentioned herein.

Furthermore, "portions" as described herein may be functionally equivalents. Preferably these portions satisfy the identity (relative to a comparable region) or hybridizing conditions mentioned herein. Preferably nucleic acid molecules of the invention, including portions and nucleotide sequences including the above described flanking sequences, preferably encode acidic polypeptides as described hereinbefore.

Nucleic acid molecules according to the invention and for use according to the invention may be single or double stranded DNA, cDNA or RNA, preferably DNA and include degenerate, substantially identical and hybridizing sequences as described above. Ideally however the molecules are DNA or cDNA.

The polypeptides of the invention, or for use according to the invention, include those which are modified without affecting the sequence of the polypeptide, e.g. by chemical modification, including by deglycosylation or glycosylation. Such polypeptides may be prepared by post-synthesis/isolation modification of the polypeptide without affecting functionality, e.g. certain glycosylation, methylation etc. of particular residues.

The polypeptides of the invention, or for use according to the invention, may also take the form of peptidomimetics which may be considered derivatives in which the functional features of the polypeptide are retained but are presented in the context of a different, e.g. non-peptide structure. Such peptidomimetics have successfully been developed and used for other particularly medical applications.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudopeptides and cyclic peptides. Structural elements considered redundant for the function of the peptide may be minimized to retain a scaffold function only or removed where appropriate.

When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the polypeptides of the invention, or for use according to the invention, are retained. The peptidomimetics are referred to as being "derivable from" a certain polypeptide sequence. By this it is meant that the peptidomimetic is designed with reference to a defined polypeptide sequence, such that it retains the structural features of the peptide which are essential for its function. This may be the particular side chains of the polypeptide, or hydrogen bonding potential of the structure. Such features may be provided by non-peptide components or one or more of the amino acid residues or the bonds linking said amino acid residues of the polypeptide may be modified so as to improve certain functions of the polypeptide such as stability or protease resistance, while retaining the structural features of the polypeptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |

TABLE 1-continued

| Non-conventional amino acid | Code | Non-conventional amino acid | Code |
|---|---|---|---|
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

Non-standard amino acids which may be used include conformationally restricted analogs, e.g. such as Tic (to replace F), Aib (to replace A) or pipecolic acid (to replace Pro).

The polypeptides and nucleic acid molecules discussed above also include derivatives which have been modified, e.g. to facilitate their use in pharmaceutical applications (discussed below), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned polypeptides or nucleic acid molecules. Nucleic acid molecules may be present in a viral carrier as described hereinafter.

The polypeptides also encompass derivatives in the form of "pro-drugs" or "pro-peptides" such that the added component may be removed by cleavage once administered, e.g. by cleavage of a substituent added through esterification which may be removed by the action of esterases. Such pro-drugs include native precursors of the naturally occurring proteins which are cleaved e.g. by proteolysis to yield the polypeptide of interest. Such precursors may be inactive in the precursor form but may be activated by proteolytic cleavage. However, any sequences which when added to the central polypeptide form a contiguous amino acid sequence are limited to flanking sequences as described above. Alternatively they may have longer flanking sequences providing they do not extend to molecules which are the native sequence from which the VAP fragment is derived (e.g. SEQ ID Nos. 5-8 in relation to the amino acid sequences and SEQ ID Nos. 13-16 for the nucleotide sequences) or a sequence with at least 50, 60, 70, 80 or 90% sequence identity to that sequence in the comparable portion.

The nucleic acid molecules of the invention, or for use according to the invention, thus similarly encompass molecules which encode such pro-drugs or precursors. However, any sequences which when added to the central polynucleotide form a contiguous nucleotide sequence are limited to flanking sequences as described above. Alternatively they may longer flanking sequences providing they do not extend to molecules which are the native sequence from which the VAP fragment is derived or a sequence with at least 50, 60, 70, 80 or 90% sequence identity to that sequence in the comparable portion.

Modified polypeptides or nucleic acid molecules as described above may be tested to ensure that they retain functional activity relative to the unmodified molecule by determining if they have the same or similar medical or cosmetic effects.

The nucleic acid molecules described above may be operatively linked to an expression control sequence, or a recombinant DNA cloning vehicle or vector containing such a recombinant DNA molecule. This allows intracellular expression of the polypeptide of the invention, or for use according to the invention, as a gene product, the expression of which is directed by the gene(s) introduced into cells of interest. Gene expression is directed from a promoter active in the cells of interest and may be inserted in any form of linear or circular DNA vector for incorporation in the genome or for independent replication or transient transfection/expression. Suitable transformation or transfection techniques are well described in the literature. Alternatively, the naked DNA molecule may be introduced directly into the cell for the uses described herein.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules required for performance of the method of the invention as described hereinafter. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Preferred vectors include bacterial and mammalian expression vectors pGEX-KG, pEF-neo and pEF-HA. The nucleic acid molecule may conveniently be fused with DNA encoding an additional polypeptide, e.g. glutathione-S-transferase, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleotide sequences of the invention encoding the polypeptides of the invention into vector nucleic acid.

In methods as described hereinafter, the polypeptides may be administered to a cell by transfection of a cell with a nucleic acid molecule of the invention, or for use according to the invention. As mentioned above, the present invention thus extends to nucleic acid molecules consisting of, or comprising, a sequence which encodes the polypeptides of the invention as described herein and their use in methods described herein. Preferably said nucleic acid molecules are contained in a vector, e.g. an expression vector.

Nucleic acid molecules of the invention, or for use according to the invention, preferably contained in a vector, may be introduced into a cell by any appropriate means. Suitable transformation or transfection techniques are well described in the literature. A variety of techniques are known and may be used to introduce such vectors into prokaryotic or eukaryotic cells for expression. Preferred host cells for this purpose include insect cell lines, eukaryotic cell lines or *E. coli*, such as strain BL21/DE3. The invention also extends to transformed or transfected prokaryotic or eukaryotic host cells containing a nucleic acid molecule, particularly a vector as defined above.

A further aspect of the invention provides a method of preparing a polypeptide of the invention as hereinbefore defined, which comprises culturing a host cell containing a nucleic acid molecule as defined above, under conditions whereby said polypeptide is expressed and recovering said molecule thus produced. The expressed polypeptide forms a further aspect of the invention.

The invention also extends to a polypeptide encoded by a nucleic acid molecule as hereinbefore described. This may be produced by expression of a host cell as described above.

Cells producing and secreting polypeptides of the invention, but which have been modified relative to native cells by expression of encoding nucleic acid material, form further aspects of the invention.

The polypeptides or nucleic acid molecules used in compositions and uses of the invention as described hereinbelow may be obtained or derived from naturally occurring sources or may be generated entirely or partially synthetically.

Conveniently the polypeptides and nucleic acid molecules are isolated in accordance with the protocols described in the Examples and below or as described in Yasumasu et al., 1989, J. Biochem., 105, p 212-218 in relation to choriolysin, which is hereby incorporated by reference, particularly in relation to the isolation methodology. Such methods and the products of such methods as they relate to the VAPs described herein form further aspects of the invention.

Thus in a further aspect the present invention provides a method of isolating one or more polypeptides (VAPs or related sequences) as described herein from hatching fluid (e.g. of salmon) comprising at least the steps of:
a) suspending eggs in a minimal volume of water (e.g. less than the volume of the eggs);
b) inducing synchronized, rapid hatching of said eggs (preferably such that hatching is complete within less than 3 hours for more than 95% of the embryos);
c) filtering the hatching eggs to obtain hatching fluid;
d) adding acetone to said hatching fluid to a final concentration of 80% v/v; and
e) subjecting said fluid to low speed centrifugation wherein said polypeptide(s) is present in the pellet thus formed; and optionally
f) separating the polypeptides present in the pellet of step e) to isolate individual polypeptides, e.g. by the use of an ion-exchange column.

A preferred ion-exchange column is a DEAE-Sepharose® CL-6B column, however suitable alternatives are readily available.

Preferably said hatching fluid is from fish, especially Salmonidae, particularly Salmo, e.g. *Salmo salar* (Atlantic salmon) and *Oncorhynchus* (Pacific salmon).

The invention further extends to polypeptides prepared by the above described method.

The polypeptides or nucleic acid molecules of the invention, or for use according to the invention, are preferably substantially free of any contaminating components derived from the source material or materials used in the isolation procedure or in their synthetic preparation. Especially preferably the compound is purified to a degree of purity of more than 50 or 60%, e.g. >70, 80 or 90%, preferably more than 95 or 99% purity as assessed w/w (dry weight). Such purity levels correspond to the specific molecules of interest, but includes its degradation products. Where appropriate, enriched preparations may be used which have lower purity, e.g. contain more than 1, 2, 5 or 10% of the molecule of interest, e.g. more than 20 or 30%. The polypeptides of the invention, or for use according to the invention, may be purified by, for example, chromatography (e.g. HPLC, size-exclusion, ion-exchange, affinity, hydrophobic interaction, reverse-phase) or capillary electrophoresis.

Polypeptides of the invention, or for use according to the invention, may be generated synthetically, e.g. by ligation of smaller synthetically generated peptides or more conveniently by recombinant expression of a nucleic acid molecule encoding said polypeptide as described hereinbefore.

Nucleic acid molecules of the invention, or for use according to the invention, may be generated synthetically, e.g. by amplification of a nucleic acid sequence as described herein. The VAP polypeptides and nucleic acid molecules described herein may be used as described hereinbelow to effect various cosmetic and/or medical effects and form preferred molecules for this purpose.

In addition, longer proteins (and their encoding sequences) which include the above described fragments, such as the full-length native proteins, may be used for the processes described hereinbelow. Thus, for the uses described below the polypeptide which may be used extends to a polypeptide comprising an amino acid sequence as set forth in any one of Sequences Nos. 2-8 or a sequence which is at least 50% identical to said sequence, or a portion of any of said sequences.

The definitions as they relate to polypeptides, portions, sequence identity and functionally-equivalent proteins similarly apply and preferred sequence identity values as set forth above are also applicable. Preferably the polypeptides are fragments of the native proteins (optionally with flanking sequences) as described hereinbefore. Similarly, for the uses described below the nucleic acid molecules which may be used extend to nucleic acid molecules comprising a nucleotide sequence which encodes a polypeptide of the invention or a longer polypeptide as described above or a complementary sequence thereof. Preferably the uses are performed with fragments of the native encoding sequences (optionally with flanking sequences) as described hereinbefore.

Thus, for the uses described below the nucleic acid molecule which may be used extends to a nucleic acid molecule comprising a nucleotide sequence as set forth in any one of SEQ ID Nos. 10-16 or a sequence which is at least 50% identical to said sequence, or a sequence which hybridizes to said sequence under non-stringent binding conditions of 6×SSC/50% formamide at room temperature and washing under conditions of high stringency, e.g. 2×SSC, 65° C., where SSC=0.15 M NaCl, 0.015M sodium citrate, pH 7.2, or a sequence complementary to any of the aforesaid sequences, or a portion of any of said sequences.

As referred to hereinafter in relation to the uses of the invention, reference to polypeptides and nucleic acid molecules refers to this broader definition, i.e. not just fragments of the native molecules which optionally contain flanking sequences as described above.

In addition to the above described VAPs, it has also been found that a further protein found in fish hatching fluid has advantageous cosmetic and/or medical uses which are complementary to those of the VAPs, namely choriolysin L as discussed hereinbefore.

Thus, polypeptides or nucleic acid molecules as disclosed herein may be used ex vivo or in vitro, on animal parts or products, for example skin samples, particularly when it is contemplated that these will be reintroduced into the body from which they are derived, e.g. in the form of a skin graft.

However, the polypeptides and nucleic acid molecules as disclosed herein are preferred for use in vivo as discussed in more detail below.

Polypeptides and nucleic acid molecules as described herein have applications for the treatment of various abnormalities, disorders or conditions as described hereinafter.

The present invention thus extends to a pharmaceutical composition comprising a polypeptide or nucleic acid molecule as described hereinbefore and one or more pharmaceutically acceptable excipients and/or diluents.

Alternatively stated, the present invention provides a pharmaceutical composition comprising:

(i) a polypeptide comprising an amino acid sequence as set forth in SEQ ID No. 1 or a sequence which is at least 50% identical to said sequence, or a portion of any of said sequence;

(ii) a polypeptide comprising an amino acid sequence as set forth in SEQ ID No. 2 or a sequence which is at least 50% identical to said sequence, or a portion of any of said sequence;

(iii) a polypeptide comprising an amino acid sequence as set forth in SEQ ID No. 3 or a sequence which is at least 50% identical to said sequence, or a portion of any of said sequence; and/or (iv) a polypeptide comprising an amino acid sequence as set forth in SEQ ID No. 4 or a sequence which is at least 50% identical to said sequence, or a portion of any of said sequence;

and one or more pharmaceutically acceptable excipients and/or diluents.

In a preferred aspect, when the use of longer sequences than those presented in SEQ ID Nos. 2-4 are contemplated, in the above list, SEQ ID Nos. 2-4 may be replaced with SEQ ID Nos. 5-7, respectively and wherein SEQ ID NO: 2 can alternatively be replaced with SEQ ID NO: 8.

Preferred polypeptides are as described hereinbefore, particularly, in relation to VAPs, fragments of native sequences, optionally containing flanking sequences. References to a pharmaceutical composition herein may be read as encompassing cosmetic compositions.

Alternatively, or additionally said composition may comprise the encoding sequence of said polypeptide, i.e. nucleic acid molecules as described hereinbefore (e.g. (v) one or more nucleic acid molecules encoding a polypeptide as set forth in any of (i) to (iv) above or a complementary sequence thereof). Preferred nucleic acid molecules are as described hereinbefore, i.e. with reference to SEQ ID Nos. 9-16, preferably 9-12.

In a preferred aspect, said composition comprises a combination of said components, e.g. components (ii) to (iv) above (i.e. all the described VAPs) or any combination of said 4 components listed above.

By "pharmaceutically acceptable" or "physiologically acceptable" is meant that the ingredient must be compatible with other ingredients in the composition as well as physiologically acceptable to the recipient.

The active ingredient for administration may be appropriately modified for use in a pharmaceutical composition. For example the compounds used in accordance with the invention may be stabilized against degradation by the use of derivatives as described above.

The active ingredient may also be stabilized in the compositions for example by the use of appropriate additives such as salts or non-electrolytes, acetate, EDTA (for VAPS and related polypeptides), citrate (for VAPs and related polypeptides), Tris, phosphate or acetate buffers, mannitol, glycine, HSA (human serum albumin) or polysorbate.

The nucleic acid molecule or polypeptide as described herein may be present in said compositions as the sole active ingredient or may be combined with other ingredients, particularly other active ingredients, e.g. to augment the therapeutic effect or to make the composition more appealing to the consumer. Said other component may be one of the 4 optional components described above or an alternative component.

The composition comprising one or more polypeptides or nucleic acid molecules described herein may also comprise impurities, e.g. after the preparation of said one or more polypeptides or nucleic acid molecules of the invention from natural sources. In compositions comprising said one or more polypeptides or nucleic acid molecules as described herein, each of said polypeptide(s) or nucleic acid molecule(s) may be present in the range 0.0001 to 30% w/w of the pharmaceutical composition. Preferably said polypeptide(s) or nucleic acid molecule(s) is present at a range of 0.01-10% or as described hereinafter.

In a further aspect of the invention, the compositions as described herein are for use in therapy.

As mentioned above, the polypeptides and nucleic acid molecules of the invention exhibit therapeutic properties in the treatment of skin abnormalities, disorders or conditions, by moisturizing and/or exfoliating the skin.

Preferred skin abnormalities, conditions or disorders to be treated are dry skin, skin in which the horny layer is thicker than desirable, e.g. in hyperkeratosis conditions, or skin with undesirable pigmentation in the epidermis, e.g. liver, age, sun or brown spots. The treatments may be cosmetic, e.g. the treatment of normal but dry skin or thickened skin (such as calluses, corns or hyperkeratotic warts) or treatment of pigmentation disorders, such as liver spots, or therapeutic, e.g. to treat acne, eczema, psoriasis or warts resulting in pain.

As referred to herein a "disorder" refers to an underlying pathological disturbance in a symptomatic or asymptomatic organism relative to a normal organism, which may result, for example, from infection or an acquired or congenital genetic imperfection. An "abnormality" or "condition" refers to an irregularity or defect in the skin relative to normal optimal skin but which is not as the result of a pathological disturbance. The defect/irregularity may instead result from age, injury, environmental factors, hormone levels, medication, externally applied or ingested materials, genetic conditions or a variety of other factors which leads to abnormal functioning of the skin resulting in irregularities.

The disorder, abnormality or condition may be merely cosmetic or non-cosmetic requiring medical treatment, or a combination thereof.

As referred to herein "cosmetic" is intended to refer to a treatment which does not cure, treat or prevent a disease or disorder, but instead serves as a skincare product or to modify or improve the appearance of the skin, e.g. the colour, texture or moisture content of the skin.

A "non-cosmetic" (or medical) ingredient used in medical treatments as described herein serves to cure, mitigate, treat or prevent one or more symptoms of the disorder, e.g. pain or discomfort.

The basis of the treatments described herein is the skin moisturizing and exfoliating effects of the VAPs and/or choriolysin as disclosed herein. These effects have been shown in the Examples provided herein.

Thus treatments based on the moisturizing and/or exfoliation properties of VAPs and/or choriolysin are contemplated.

The invention thus provides a cosmetic or non-cosmetic method of exfoliating and/or moisturizing skin of an animal, wherein a polypeptide, nucleic acid molecule or pharmaceutical composition as described hereinbefore is administered to said animal.

Thus, with reference to the above, the present invention provides a cosmetic or non-cosmetic method of exfoliating and/or moisturizing skin of an animal, wherein a polypeptide, nucleic acid molecule or pharmaceutical composition is administered to said animal, wherein said polypeptide comprises an amino acid sequence as set forth in any one of Sequences Nos. 1-8 (preferably 1-4) or a sequence which is at least 50% identical to said sequence, or a portion of any of said sequences; said nucleic acid molecule encodes said polypeptide or is a complementary sequence thereof (e.g. a nucleotide sequence as set forth in any one of SEQ ID Nos. 9-16 (preferably 9-12) or a sequence which is at least 50% identical to said sequence, or a sequence which hybridizes to said sequence under non-stringent binding conditions of 6×SSC/50% formamide at room temperature and washing under conditions of high stringency, e.g. 2×SSC, 65° C., where SSC=0.15 M NaCl, 0.015M sodium citrate, pH 7.2, or a sequence complementary to any of the aforesaid sequences, or a portion of any of said sequences) and said pharmaceutical composition comprises one or more of said polypeptides or nucleic acid molecules and one or more pharmaceutically acceptable excipients and/or diluents.

As described above and referred to herein, the above described polypeptide and nucleotide sequences defined by reference to SEQ ID Nos. 2-8 and 10-16 are VAPs or related sequences and those defined by reference to SEQ ID Nos. 1 and 9 are choriolysin or related sequences.

As referred to herein, "exfoliating" refers to removing superficial cells of an epithelium surface which in skin equates to scaling or desquamation of the horny layer of the epidermis. "Moisturizing" as referred to herein covers moisturizers which prevent loss of water from the skin as well as moisturizers (humectants) that attract and retain water when applied to the skin and emollients (which improve defective desquamation).

Alternatively stated, the present invention provides a polypeptide, nucleic acid molecule or pharmaceutical composition as described herein for use in exfoliating and/or moisturizing skin of an animal. (The compound or composition may alternatively be used to prepare a medicament for that purpose.)

As mentioned above, such exfoliating and/or moisturizing properties are advantageous for treating or preventing a variety of skin abnormalities, disorders or conditions.

In a preferred aspect, the skin abnormality, condition or disorder to be treated or prevented is dry skin. This may be treated by moisturizing and/or exfoliation.

"Dry skin" as referred to herein refers to an epidermis that lacks moisture or sebum, often characterized by a pattern of fine lines, scaling, and itching. Dry skin can occur as a skin condition in itself (e.g. due to age, heat/cold/dry damage) or may be the symptom of a skin disorder or condition such as sun-damage, eczema, contact dermatitis, psoriasis or ichthyosis (an inherited condition causing marked flaking of the skin).

In a further preferred aspect, the abnormality, condition or disorder to be treated or prevented is thickened horny layers of the skin. This may be treated by moisturizing and/or exfoliation.

Such thickened horny layers of the skin may occur in conditions such as calluses or corns which are protective pads made up of the thickened upper layer of skin due to repeated rubbing of the area or warts on the skin. Such methods may also be used to treat or prevent acne which involves keratinisation in its pathology. The thickened horny layers of the skin may be the condition itself or may be a symptom of a skin condition or disorder.

In a further preferred aspect, the abnormality, condition or disorder to be treated or prevented is a pigmentation disorder or abnormality of the skin. This may be treated by exfoliation.

Pigmentation disorders or abnormalities of the skin may occur as a result of age, hormonal changes, genetic factors, disease or sun or other damage. Altered pigmentation may result from a local excess of melanocytes or increases in melanocyte activity, or both. Pigmentation disorders include liver, sun or age spots (solar lentigo) and other blemishes such as freckles.

Alternatively stated, the present invention thus provides a cosmetic or non-cosmetic method of treating or preventing a condition or disorder of the skin of an animal wherein said skin is abnormally dry, the horny layer of the skin is abnormally thickened or the skin has a pigmentation disorder, wherein a polypeptide, nucleic acid molecule or pharmaceutical composition as described hereinbefore is administered to said animal. Said conditions or disorders are preferably as described hereinbefore.

As referred to herein "abnormal" is determined relative to normal optimum skin, i.e. healthy, hydrated, normally pigmented and non-aged skin.

In a further alternative statement, the invention provides a polypeptide, nucleic acid molecule or pharmaceutical composition as described herein for use in a cosmetic or non-cosmetic method of treating or preventing a condition or disorder of the skin of an animal wherein said skin is abnormally dry, the horny layer of the skin is abnormally thickened or the skin has a pigmentation disorder. (The compound or composition may alternatively be used to prepare a medicament for that purpose.)

In a preferred aspect the medical and/or cosmetic uses are achieved by topical administration to the skin.

Preferably, for medical or cosmetic indications reliant, at least in part, on the exfoliation effects of the active ingredients, the pharmaceutical compositions used for this purpose comprise one or more VAPs (or their related sequences as described herein) and/or choriolysin (or its related sequences as described herein).

Preferably, for medical or cosmetic indications reliant, at least in part, on the moisturizing effects of the active ingredients, the pharmaceutical compositions used for this purpose comprise one or more VAPs (or their related sequences as described herein).

Thus in a particularly preferred aspect, one or more VAPs (or their related sequences as described herein) and/or choriolysin (or its related sequences as described herein) may be used for treating disorders in which the skin is abnormally dry, the horny layer of the skin is abnormally thickened or in which a pigmentation defect is present, e.g. calluses, corns, warts, eczema, contact dermatitis, psoriasis, ichthyosis, acne and liver spots.

In a further particularly preferred aspect, one or more VAPs (or their related sequences as described herein) may be used for treating disorders in which the skin is abnormally dry.

As used herein, "treating" refers to the reduction, alleviation or elimination, preferably to normal levels, of one or more of the symptoms or effects of said condition or disorder e.g. presence or extent of dry or thickened skin, extent or area of pigmentation, itching or pain etc. relative to the symptoms or effects present on a different part of the body of said individual where the skin does not suffer from said condition or disorder and not subject to said treatment or in a corresponding normal individual not subject to said treatment.

"Preventing" refers to absolute prevention, or reduction or alleviation of the extent or timing (e.g. delaying) of the onset of that symptom or effect. For example conditions typified by dry, thickened or abnormally pigmented skin may be prevented by regular application of compositions of the invention before the appearance of such a condition.

Preferably said treatments are achieved using polypeptide methods of the invention. However, the use of the encoding polynucleotides are also contemplated. This may be achieved, for example, by gene therapy methods, e.g. use of sense sequences to allow expression of the desired molecules in the skin.

The method of treatment or prevention according to the invention may advantageously be combined with administration of one or more active ingredients which are effective in treating or preventing the disorders or conditions and/or to achieve moisturization or exfoliation. Thus, pharmaceutical compositions of the invention may additionally contain one or more of such active ingredients.

According to a yet further aspect of the invention we provide products containing one or more polypeptides or nucleic acid molecules as herein defined and optionally one or more additional active ingredients as a combined preparation for simultaneous, separate or sequential use in human or animal therapy, preferably as described herein.

The compositions of the invention may be formulated in a conventional manner with one or more physiologically acceptable carriers, excipients and/or diluents, according to techniques well known in the art using readily available ingredients.

Thus, the active ingredient may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions of the invention may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

These particles may carry appropriate surface molecules to improve circulation time (e.g. serum components, surfactants, polyoxamine908, PEG etc.) or moieties for site-specific targeting, such as ligands to particular cell borne receptors. Appropriate techniques for drug delivery and for targeting are well known in the art and are described in WO99/62315.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Compositions may be for topical (i.e. to the skin), oral or parenteral administration, e.g. by injection.

Topical compositions and administration are however preferred, and include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional pharmaceutical or cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The concentration of active ingredient in compositions of the invention, depends upon the nature of the compound used (i.e. the polypeptide or nucleic acid molecule), the mode of administration, the course of treatment, the age and weight of the patient, the medical indication, the body or body area to be treated and may be varied or adjusted according to choice. Generally however, concentration ranges for the compound described herein is 0.0001, 0.0005, 0.001 or 0.01 to 25%, e.g. 0.0005-15%, e.g. 0.01 to 10%, such as 0.1 or 0.5 to 5, e.g. 1-5% (w/w of the final preparation for administration, particularly for topical administration).

When more than one compound is present, e.g. 3 VAPs (or related molecules) as described herein, each compound may be present in the amounts described above. Said concentrations are determined by reference to the amount of the compound itself and thus appropriate allowances should be made to take into account the purity of the composition. Effective single doses for VAPs (and related molecules) may lie in the range of from 0.1-100 mg/cm$^2$/day, preferably 0.1-10 mg/cm$^2$/day, when applied topically, depending on the animal being treated, taken as a single dose. For choriolysin (and related molecules) effective single doses may lie in the range of from 0.1-100 mU/cm$^2$/day, preferably 0.5-10, e.g. 1-5 mU/cm$^2$/day.

The administration may be by any suitable method known in the medicinal arts, including for example oral, intestinal, percutaneous, buccal, rectal or topical administration or administration by inhalation. The preferred administration forms will be administered orally, or most preferably topically. As will be appreciated oral administration has its limitations if the active ingredient is digestible. To overcome such problems, ingredients may be stabilized as mentioned previously.

It will be appreciated that since the active ingredient for performance of the invention takes a variety of forms, e.g. nucleic acid molecule (which may be in a vector) or polypeptide, the form of the composition and route of delivery will vary. Preferably however liquid solutions, creams or suspensions would be employed, particularly e.g. for oral delivery or topical administration.

Either the polypeptide or nucleic acid molecules of the invention may be used for the above mentioned medical indications. In the latter gene therapy methods, the nucleic acid molecules are preferably provided in vectors which are suitable for transfection/transformation as described above, e.g. viral vectors such as adenovirus using gene therapy methods known in the art for medical applications.

Animals to which the compositions may be applied or administered include mammals, reptiles, birds, insects and fish particularly during fish aquaculture (e.g. salmon or cod). Preferably the animals to which the compositions of the invention are applied are mammals, particularly primates, domestic animals, livestock and laboratory animals. Thus preferred animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows:

FIG. 1 shows isoelectric focussing of the VAPs after their purification;

EXAMPLE 1

Identification and Characterization of VAPs

Protein Isolation

Figure 2A:
FIG. 2 shows the effects of Atlantic salmon VAPs on human epithelium in which A and B show the skin culture exposed to VAPs, and C shows the control skin culture.

During the course of analyzing hatching fluid components of Atlantic salmon, new proteins present in the hatching fluid were identified.

A method for preparing partially hatching fluid (from which zonase may be prepared) which may be used as the starting material for isolating the VAPs of the invention (or their precursor sequences) is provided in WO99/29836 which is hereby incorporated by reference (particularly Example 1 of the described method, but optionally without the urea step).

Thus, the following method has been used for isolation. VAPs were isolated from hatching fluid (crude or filtered through 0.45 μm filters). Subsequently the VAPs were precipitated by adding 4× volumes of acetone at room temperature or at 4° C. After 20-30 minutes the precipitated VAPs were collected as a pellet after centrifugation at low speed (around 5000×g) and resuspended in the appropriate buffer (e.g. 10 mM TrisHCl, pH8.0 or PBS).

FIG. 1 shows 2D PAGE of the VAPs after their purification as described above.

Sequence Analysis

The newly identified VAPs were subjected to characterization by MS analysis of the trypsinized spots. The MS analysis was MALDI-TOF-TOF (Matrix assisted laser desorption/ionization. Time of flight ×2).

The following results were obtained for the best match as reflected by the top score.

VAP I gi|185133695 Mass: 49859 Score: 419 Expect: 8.2e-36 Queries matched: 7 eggshell protein [*Salmo salar*]

| Observed | Mr(expt) | Mr(calc) | Delta | Start | - | End | Miss | Ions | Peptide | SEQ ID No |
|---|---|---|---|---|---|---|---|---|---|---|
| 1105.6858 | 1104.6785 | 1104.5928 | 0.0857 | 126 | - | 135 | 0 | 56 | K.DGQFVVVVSR.D | 17 |
| 1439.6891 | 1438.6818 | 1438.6300 | 0.0519 | 210 | - | 220 | 0 | 102 | R.DSHYDLVFQCR.Y | 18 |
| 1538.8765 | 1537.8693 | 1537.8239 | 0.0453 | 221 | - | 234 | 0 | — | R.YTGTSVETLVIEVK.T | 19 |
| 1785.9341 | 1784.9269 | 1784.8767 | 0.0501 | 193 | - | 209 | 0 | — | R.MSSSYVVGIGPFGDITR.D R.MSSSYVVGIGPFGDITR.D | 20 |
| 1801.9253 | 1800.9180 | 1800.8717 | 0.0464 | 193 | - | 209 | 0 | 130 | + Oxidation (M) | 21 |
| 2023.1099 | 2022.1027 | 2022.0569 | 0.0458 | 118 | - | 135 | 1 | 93 | K.TVTVQCTKDGQFVVVVSR.D | 22 |
| 2311.1242 | 2310.1169 | 2310.0686 | 0.0484 | 173 | - | 192 | 0 | — | K.VTECGTVVTEEPDTIVYENR.M | 23 |

VAP II gi|158132194 Mass: 59145 Score: 502 Expect: 4.1e-44 Queries matched: 12 choriogenin H beta [*Oncorhynchus masou*]

| Observed | Mr(expt) | Mr(calc) | Delta | Start | - | End | Miss | Ions | Peptide | SEQ ID No |
|---|---|---|---|---|---|---|---|---|---|---|
| 1089.6560 | 1088.6488 | 1088.5979 | 0.0509 | 211 | - | 220 | 0 | 52 | K.DGQFVVVVAR.D | 24 |
| 1198.6832 | 1197.6759 | 1197.6717 | 0.0042 | 385 | - | 395 | 0 | 80 | R.TDPNIVLTLGR.C | 25 |
| 1346.7405 | 1345.7333 | 1345.7354 | -0.0021 | 370 | - | 380 | 1 | 48 | K.VLRDPVYTEVR.I | 26 |
| 1432.6125 | 1431.6052 | 1431.6089 | -0.0037 | 295 | - | 305 | 0 | 62 | R.DSQYDLTFQCR.Y | 27 |
| 1688.7701 | 1687.7629 | 1687.7772 | -0.0143 | 450 | - | 463 | 0 | — | K.MFTFVDPMSMTPLR.E + Oxidation (M) | 28 |
| 1704.7646 | 1703.7573 | 1703.7721 | -0.0149 | 450 | - | 463 | 0 | — | M.MFTFVDPMSMTPLR.E + 2 Oxidation (M) | 29 |
| 1720.7581 | 1719.7508 | 1719.7671 | -0.0162 | 450 | - | 463 | 0 | — | K.MFTFVDPMSMTPLR.E + 3 Oxidation (M) | 30 |
| 1772.8510 | 1771.8438 | 1771.8563 | -0.0126 | 278 | - | 294 | 0 | 93 | R.MSSSYQVGVGPFGSITR.D | 31 |
| 1788.8447 | 1787.8374 | 1787.8513 | -0.0138 | 278 | - | 294 | 0 | (88) | R.MSSSYQVGVGPFGSITR.D + Oxidation (M) | 32 |
| 1977.0356 | 1976.0284 | 1976.0514 | -0.0230 | 203 | - | 220 | 1 | 129 | K.AVTVQCTKDGQFVVVVAR.D | 33 |
| 2361.0236 | 2360.0163 | 2360.0512 | -0.0349 | 258 | - | 277 | 0 | — | K.VTECGTVMTEETDTIIYENR.M | 34 |
| 2377.0210 | 2376.0137 | 2376.0461 | -0.0324 | 258 | - | 277 | 0 | — | K.VTECGTVMTEETDTIIYENR.M + Oxidation (M) | 35 |

VAP III
Comparison to Peptides of Choriogenin (*Oncorhynchus masou*)

| Start-End | Observed | Mr(expt) | Mr(calc) | Delta | Miss | Sequence | SEQ ID No |
|---|---|---|---|---|---|---|---|
| 103-115 | 1572.7675 | 1571.7602 | 1571.7184 | 0.0418 | 1 | R.AECRENMVHVEAK.H (No match) | 36 |
| 103-115 | 1588.7668 | 1587.7596 | 1587.7133 | 0.0462 | 1 | R.AECRENMVHVEAK.H Oxidation (M) (No match) | 37 |
| 188-201 | 1733.8167 | 1732.8094 | 1732.7661 | 0.0434 | 0 | R.TNDAMINIECHYPR.K (No match) | 38 |
| 188-201 | 1749.8474 | 1748.8401 | 1748.7610 | 0.0791 | 0 | R.TNDAMINIECHYPR.K Oxidation (M) (Ions s-core 82) | 39 |
| 222-232 | 1421.7118 | 1420.7045 | 1420.6696 | 0.0348 | 0 | K.YAEELLYFSMR.L (No match) | 40 |
| 222-232 | 1437.7161 | 1436.7088 | 1436.6646 | 0.0443 | 0 | K.YAEELLYFSMR.L Oxidation (M) (Ions score 33) | 41 |
| 233-242 | 1312.6294 | 1311.6221 | 1311.5918 | 0.0304 | 0 | R.LMTADWQYER.A (No match) | 42 |
| 233-242 | 1328.6293 | 1327.6220 | 1327.5867 | 0.0354 | 0 | R.LMTADWQYER.A Oxidation (M) (Ions score 37) | 43 |
| 269-287 | 2130.1112 | 2129.1039 | 2129.0575 | 0.0464 | 0 | R.IFVDSCVATLEPNINANPR.Y (Ions score 143) | 44 |
| 302-312 | 1278.6242 | 1277.6169 | 1277.5645 | 0.0524 | 0 | K.MTGSHSQFMPR.S (No match) | 45 |
| 318-326 | 1172.6300 | 1171.6228 | 1171.6026 | 0.0202 | 0 | K.LYFQVEAFR.F (Ions score 78) | 46 |

From the above results, the sequences of the VAPs were generated by identifying peptides in the VAP sequence by MS and then inserting the intervening sequences using relevant portions of the known native sequence to which the comparison was made. The VAP sequences identified by this process are set out in SEQ ID Nos. 2-4 and the native sequences against which they were compared are provided in SEQ ID Nos. 5-8.

EXAMPLE 2

Medical/Cosmetic Applications of VAPs in vitro

Materials and Methods

The following studies were carried out using the Atlantic salmon VAPs prepared as described in Example 1.

Differentiated human skin epithelium cultures were obtained from SkinEthics (Nice, France) at day 16 after seeding onto plastic growth substrata with micropores allowing nutrients access to the epithelial tissue from below. Such cultures exhibit normal skin morphology after differentiation during the culturing period at 37° C. These cultures were maintained for two more days in vitro so that the upper stratum corneum was exposed to air, and stratum basalis to the growth substratum.

Parallel cultures were moved to 30° C. moist atmosphere and presented with a medium Ca, Mg-containing phosphate-buffered saline for 6 hours with or without the presence of VAPs at 0.5 mg/ml (measured at OD280). Cultures were fixed in formalin and embedded in paraffin according to standard procedures, and stained with hematoxylin/eosin.

Results

A. Moisturizing Effects

Figure 2B:
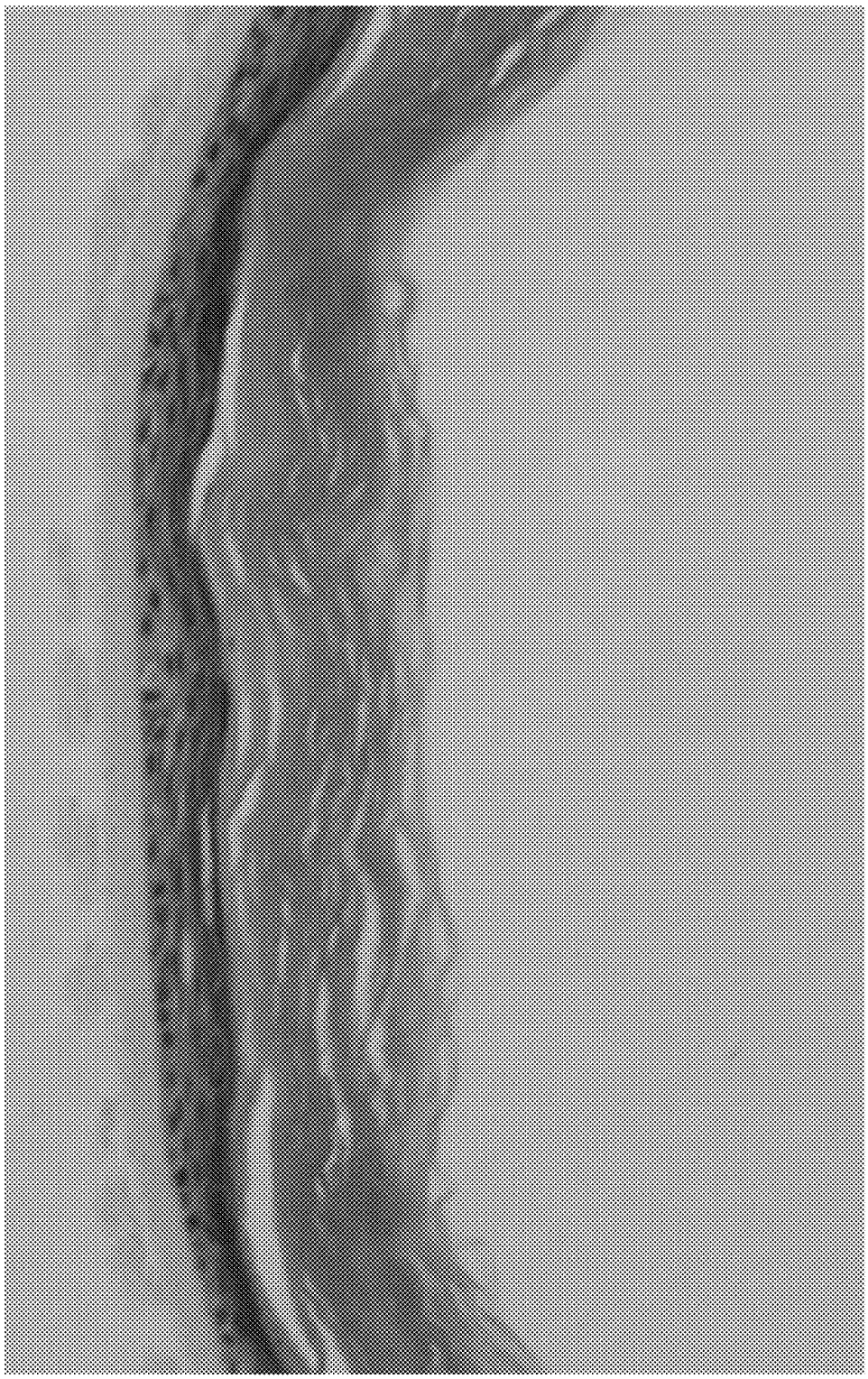
Figure 2C:

The results are shown in FIG. 2A-C in which A and B show the skin culture exposed to VAPs and C shows the control skin culture. These figures show that the VAPs cause the skin stratum corneum laminae to separate, thus "delamination" occurs. The laminae do not detach, or exfoliate, they simply separate from each other.

This separation is caused by highly charged amphiphilic proteins which intercalate in the stratum corneum, and which due to their amphiphilic character carry water to separate the skin laminae. The water is therefore piggybacked into the stratum corneum by the VAPs reducing trans-epidermal water loss (TEWL).

EXAMPLE 3

Medical/Cosmetic Applications of Choriolysin L in vitro

Materials and Methods

The following studies were carried out using the Atlantic salmon choriolysin L prepared as described in Yasumasu et al., 1989, supra, from salmon hatching fluid.

The human skin epithelium cultures were prepared as described in EXAMPLE 2 and choriolysin L from Salmon hatching fluid was applied at 0.15 mU/ml for 6 hours at 30° C.

Results

A. Exfoliation Effects

Figure 3A:
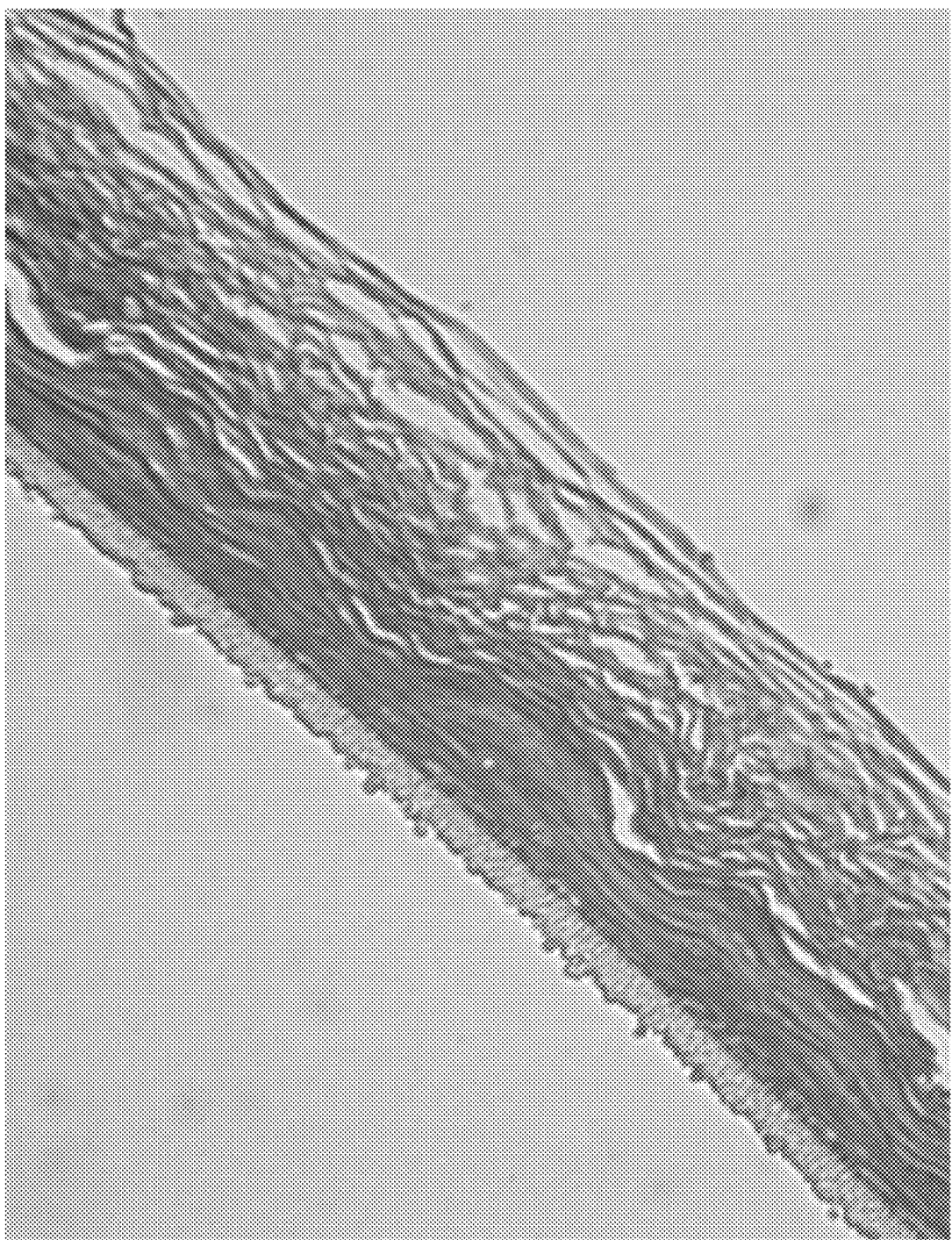
FIG. 3 shows the effects of Atlantic salmon choriolysin L on human epithelium in which A shows the skin culture exposed to choriolysin L, and B shows the control skin culture.
Figure 3B:

The results are shown in FIGS. 3A and B in which A shows the skin culture exposed to salmon choriolysin L and B shows the control skin culture. The results show that choriolysin L causes delamination and rupture of skin lamellae.

Exfoliation may also be analysed by assessing the supernatant of skin cultures to assess the amount of epithelial cells which are removed from the skin cultures during treatment. As choriolysin L is inhibited by 1 mM EDTA, its effects can be readily inhibited to prove its action on the skin.

EXAMPLE 4

Medical/Cosmetic Applications of VAPs and Choriolysin L in vivo

Cosmetic Applications

Individuals suffering from dry skin and/or skin requiring exfoliation (e.g. calluses or corns) are administered cosmetic or placebo creams as described below. Treatment is repeated periodically, e.g. every 8 hours.

The effects of the cream on the skin are analysed based on qualitative effects such as appearance and feel (e.g. itchiness) or may be analyzed more quantitatively, e.g. on water content or thickness.

Medical Applications

Individuals suffering from a condition or abnormality of the skin such as acne, eczema or psoriasis are administered treatment or placebo creams as described below. Treatment is repeated periodically, e.g. every 8 hours.

The effects of the cream on the skin are analysed based on qualitative effects such as appearance, feel (e.g. pain) or colour or may be analyzed more quantitatively, e.g. on size of the remaining abnormality, extent of inflammation or thickness.

Placebo Cream:

| Name | INCI Name | % | Phase/Temp (° C.) |
|---|---|---|---|
| Cetiol V | Decyl Oleate | 4 | A/75 |
| Dynacerin 660 | Oleyl Erucate | 6 | A/75 |
| CUTINA GMS V | Glyceryl stearate | 3 | A/75 |
| Cire da lanol CTO | Cetearyl alcohol & Cteareth 33 | 2 | A/75 |
| Nacol 16-95 | Cetyl alcohol | 1 | A/75 |
| Edenor L2 SM GS | Stearic acid & Palmitic acid | 3 | A/75 |
| Nacol 18-94 | Cetyl alcohol | 1 | A/75 |
| Radia 7730 | Isopropyl myristate | 4 | A/75 |
| dH$_2$O | | 25 | B/75 |
| Glycerin 4810 | Glyerin | 3 | B/75 |
| Optiphen | | 1 | B/75 |
| Triethanolamine 85% | | 0.4 | B/75 |
| dH$_2$O | | 46.3 | C/75 |
| Nipa Biopure 100 | Imidazolodinyl urea | 0.3 | C/25 |

Cosmetic/Treatment Cream with 10% Active Ingredient:

| Name | INCI Name | % | Phase/Temp (° C.) |
|---|---|---|---|
| Cetiol V | Decyl Oleate | 4 | A/75 |
| Dynacerin 660 | Oleyl Erucate | 6 | A/75 |
| CUTINA GMS V | Glyceryl stearate | 3 | A/75 |
| Cire da lanol CTO | Cetearyl alcohol & Cteareth 33 | 2 | A/75 |
| Nacol 16-95 | Cetyl alcohol | 1 | A/75 |
| Edenor L2 SM GS | Stearic acid & Palmitic acid | 3 | A/75 |
| Nacol 18-94 | Cetyl alcohol | 1 | A/75 |
| Radia 7730 | Isopropyl myristate | 4 | A/75 |
| dH$_2$O | | 25 | B/75 |
| Glycerin 4810 | Glyerin | 3 | B/75 |
| Optiphen | | 1 | B/75 |
| Triethanolamine 85% | | 0.4 | B/75 |
| dH$_2$O | | 36.3 | C/75 |
| Nipa Biopure 100 | Imidazolodinyl urea | 0.3 | C/25 |
| VAP and/or choriolysin L | | 10 | 25 |

Sequences:

```
SEQ ID No. 1:
Choriolysin L - Atlantic salmon
MDHRPTLSLL LLLLLLGLSQ ASGNEFHDEP DHVSITSVIL KSNNGTNELL

LDGDILAPRT RNAMKCFSSQ YSCLWKKSSD GLVYVPYILS AVYSSLEVET IETAMKYFQG

KTCIRFIPRK TQTAYLDIQS SGGCFGTVGT VGDRQTLSLA

QFGCVQHGII QHELLHALGF YHEHNRSDRE QYIRINWQYI YDYAVGNFQK EDTNNLHTAY

DYSSVMHYDR TAYTNDYGKE TITPIPDPSV AIGQRLGMSD IDVLKVNKLY QC

SEQ ID No. 2:
VAP I - Atlantic salmon
TVTVQCTKDG QFVVVVSRDA TLPNLELDSI SLLGANGAHC TPVGTTSAFA IYQFKVTECG

TVVTEEPDTI VYENRMSSSY VVGIGPFGDI TRDSHYDLVF QCRYTGTSVE TLVIEVK

SEQ ID No. 3:
VAP II - Salmon
AVTVQCTKDG QFVVVVARDA TLPSLELDSI SLLGTNGPHC HAIGTTSVFA

IYQFKVTECG TVMTEETDTI IYENRMSSSY QVGVGPFGSI TRDSQYDLTF

QCRYKGSTIV AVVIDVKPVP PPNPDIAPGP LTVELRLGSG TCLTKGCNEE EVAYTSYYTE

ADYPVTKVLR DPVYTEVRIL ARTDPNIVLT LGRCWATTNP NPLSLPQWDL LIDGCPYQDD

RYLTTPINVG PSSGLSFPTH YRRFVLKMFT FVDPMSMTPL R

SEQ ID No. 4:
VAP III - Salmon
AECRENMVHV EAKHDLLGIG QLIQLEDLTL GDCPMSGFDN INQVLIFESP LQSCGSQLRM

TTNSLIYIFT LYYKPKPLAN TPLIRTNDAM INIECHYPRK HNVSSLALIP TWTPFSAAKY

AEELLYFSMR LMTADWQYER AGNMYVLGDM VNIEASVMQY FHVPLRIFVD

SCVATLEPNI NANPRYAFIE NHGCLIDAKM TGSHSQFMPR SADYKLYFQV EAFR

SEQ ID No. 5:
Full length zr-protein - Atlantic salmon
MKWSAVCLVA VATLGWLCDA QNFLEKPGWP PIQTPPSWPP QTPQRPVQPL

PQRPAQPFLQ KPAQPIPQRI PYTEDDTKQT CEVVDKDKVS CGLSGITAAQ
```

```
CQAISCCFDG RMCFYGKTVT VQCTKDGQFV VVVSRDATLP NLELDSISLL

GANGAHCTPV GTTSAFAIYQ FKVTECGTVV TEEPDTIVYE NRMSSSYVVG IGPFGDITRD

SHYDLVFQCR YTGTSVETLV IEVKTYPNPN PVVTVDAVLN VELRLANGRC

LSKGCDEMQE AYTSYYTVAD YPVTKVLRDP VYAEVRILGM TDPNVVLTLE

QCWATIDPTG DRLPRWDLLV NGCPYQDDRY LTVPIASDSS YIPPGEFLSH

YKRFVFKMFT FVDPTSMVPL QENVYIHCRA TVCHALAGSC EQRCNRQRRD

LSAQGQKKTK GDVVVSSQKV IMIDPSLYA

SEQ ID No. 6:
Full length choriogenin H - Pacific salmon
MKWSAVCLVA VATLGWLCDA QIYLEKPGWP PIQTPASWPA QPPEKPVQPP

QRPAQPPQWP AQPPQWPAQP PQRPAQPPQR PAQTQQWPGQ PPQRPAQPPQ

WPAQPPQRPA QPPQRPAQPP QRPAQPPPRP AQPPQWPVHP PQWPVQPGTP

LQRPKFPSDP GSKQSCDVDS QHKVQCGLPD ITAAHCDAIN CCFDGRMCFY

GKAVTVQCTK DGQFVVVVAR DATLPSLELD SISLLGTNGP HCHAIGTTSV FAIYQFKVTE

CGTVMTEETD TIIYENRMSS SYQVGVGPFG SITRDSQYDLTFQCRYKGST IVAVVIDVKP

VPPPNPDIAP GPLTVELRLG SGTCLTKGCN EEEVAYTSYY TEADYPVTKV LRDPVYTEVR

ILARTDPNIV LTLGRCWATT NPNPLSLPQW DLLIDGCPYQ DDRYLTTPIN VGPSSGLSFP

THYRRFVLKM FTFVDPMSMT PLRETVFIHC NTAVCLPSHG DSCEPRCYRK

RRDIPAAVQK TTRIKSNLVS SGELILTDPR ELTN

SEQ ID No. 7:
Full length choriogenin L - Pacific salmon
MAMKWSVVCL VAVAMLGCLC VAQIWPPSIK PVQQPFRPNR PPPQQPQQPP

YQKPRIPPKD QTQAKQKFET PLDWTYPLDP KPEPKIIGGS EARTPVAANS

VRAECRENMV HVEAKHDLLG IGQLIQLEDL TLGDCPMSGF DNINQVLIFE SPLQSCGSQL

RMTTNSLIYI FTLYYKPKPL ANTPLIRTND AMINIECHYP RKHNVSSLAL IPTWTPFSAA

KYAEELLYFS MRLMTADWQY ERAGNMYVLG DMVNIEASVM QYFHVPLRIF

VDSCVATLEP NINANPRYAF IENHGCLIDA KMTGSHSQFM PRSADYKLYF

QVEAFRFQSQ RGSDPIIPQK TKIPFQPAAD YPATLDMIFL TCHLKATTIA FPIDFEYKAC

SFINTWREAG GNDGVCGCCD STCSNRKGRD TTTHQKPANI WEGDVQLGPI FISEKVEQ

SEQ ID No. 8:
Alternative zr-protein - Atlantic salmon
KWSYQLPQKL AQPLPQKPAQ PLPQWPVQPL PQRPAEPLPQ RPAQPLPQWP

VQPLPQRPAE PLPQRPAQPL PQRPVQPLPQ RPAQPFLQKP AQPIPQRIPY

TKDDTKQTCE VVDKDKVSCG LSGITAAQCQ AISCCFDGRM CFYGKTVTFQ

CTKDGQFVVV VSRDATLPNL ELDSISLLGA NGAHCTPVGT TSAFAIYQFK VTECGTVVTE

EPDTIVYENR MSSSYVVGIG PFGDITRDSH YDLVFQCRYT GTSVETLVIE VKTYPNPNPV

VTVDAVLNVE LRLANGRCLS KGCDEMQEAY TSYYTVADYP VTKVLRDPVY

AEVRILGMTD PNVVLTLEQC WATTDPTGDR LPRWDLLVNG CPYQDDRYLT

VPIASDSSYI PPGEFLSHYK RFVFKMFTFV DPTSMVPLQE NVYIHCRATV CHALAGSCEQ

RCNRQRRDLS AQGQKKTKGD VVVSSQKVIM IDPSLYA

SEQ ID No. 9:
Nucleotide sequence, choriolysin L, Atlantic salmon
atggaccacagaccccactcttagcctgctttctgctgctgctgctgctgggcctatcacaggccagtggaaatgagttccatgatga gccggaccatgtgtccatcacttcagtaatcctgaagtccaacaacggaaccaatgagctactgctggatggagacattctagct
```

-continued cctagaaccaggaacgccatgaagtgctttagcagccagtacagctgtctctggaagaagtcatctgacggcttggtgtacgtgc cttacatcctcagcgctgtatattccagcttggaggtagagactattgagacggccatgaagtacttccaaggcaagacctgcatc cgcttcattccacgtaagacacagactgcctacctggacattcagagcagcggcgggtgttttggtaccgtggggactgttgggg acaggcagacattgtctcttgcacagtttggctgtgttcaacatggtatcatccagcatgagctgcttcacgccctgggcttctaccac gagcacaacaggagtgaccgtgaacagtatatcaggatcaactggcaatacatctatgactacgccgttgggaacttccagaa ggaggacaccaacaacctgcacactgcatacgactactcctctgtcatgcactatgataagaaccgcttacactaacgactacgg aaaggaaaccatcactcccatcccagacccatctgtggccattggacagagactgggcatgtccgacattgatgtcctgaaggt caacaagctctaccaatgctaagaggaagagcgccattgttgaaaatgtgtgatgctggatgtgctgtcatgtgctgatgtattttatt gttggaagtttgtatgtatccttttaatcacattggtaataataaagcatggttatggtaaaaaaaaa SEQ ID No. 10:
Nucleotide sequence encoding SEQ ID No. 2, VAP I
acagtgactgtccagtgtaccaaggatggccagtttgtggtggtggtttccagggatgccactctgcccaaccttgagctagattcc atcagcctgctaggggcaaacggagcccactgcaccctgtcggcaccacatctgcctttgccatctaccagttcaaagttactg aatgtggaactgtggtgacggaggaacctgatactattgtctatgagaacaggatgtcctcttcatatgtagtggggattggacccttt cggcgacattaccagggacagccactatgacctggtcttccagtgtcggtatactgggacttccgttgagacattggttatcgaggt gaaa SEQ ID No. 11:
Nucleotide sequence encoding SEQ ID No. 3, VAP II
gcagtgactgttcagtgtaccaaggatggccagtttgtggtggtggtggccaggatgccactctgcccagcctggaactggact ccatcagcctgctggggacaaacggaccccactgccatgctattggcacaacttctgtctttgccatctaccagtttaaagtcactg aatgtggaactgtcatgacggaggaaactgatactattatctatgagaataggatgtcctcttcatatcaagtgggggttggccccttt tggctccatcaccagggacagecaatatgatctaacattccagtgcagatataagggcagtaccattgtggctgtggttattgatgt gaagccggttcctcctccaaatcctgatatagctcctggaccectcacagttgagctcagactcggcagcggaacatgccttacc aagggatgtaatgaagaggaagtggcctacacctcttactacacagaggcagactaccctgtcaccaaggtcctcagggatcct gtgtacactgaggttcgcatcctggcgaggacagatcccaacattgtgctgaccctgggtcgctgctgggctaccacaaaccca aaccctctcagcctgccccagtgggaccttctcattgatggatgtccttaccaggatgaccgttacctgaccactcccatcaatgtg ggaccctcttcgggtctgtccttcccaacccactacaggcgcttcgtccttaagatgttcacctttgtggatccaatgtctatgacccc ctgagg SEQ ID No. 12:
Nucleotide sequence encoding SEQ ID No. 4, VAP III
gctgagtgcagggagaacatggtccacgtggaagcgaagcatgacctgctggggatcggccagttgatccagctagaagacc tcactttgggagactgccctatgtctggattcgacaatatcaaccaggtgctcatctttgagtctccgctgcagtcatgtggcagcca gctaaggatgactaccaactccctcatctacatcttcactctatattacaaacccaaacctctggcaaacacccccctcatcagga caaatgacgcgatgatcaatattgagtgccactatccaaggaaacacaatgtgagcagcctggccctgatcccaacctggacc cctttctccgctgctaagtatgcagaggaactcctgtacttctccatgaggctcatgactgctgactggcagtatgagagggccggt aacatgtacgtgttgggtgatatggtgaacatcgaggcctctgtcatgcagtacttccacgttcccctgcgtatctttgtggacagctgt gtggccaccctggaacccaacataaacgccaatcccagatatgccttcattgagaatcatgggtgtctgatcgatgccaaaatga caggttcccactcccagttcatgcctcgttccgcagactacaagctgtatttccaggtggaggctttcagg SEQ ID No. 13:
Full length Nucleotide sequence encoding SEQ ID No. 5, zr-protein Atlantic salmon
atgaagtggagtgcagtttgtctagtggcagtggccacgcttggctggctgtgtgatgctcagaattcttggaaaaaccagggtgg ccacccatccagacaccaccgtcatggcctccccaaacccctcagaggcctgtccaaccccttcctcagagacctgctcaacc ctttcttcagaagcctgcccaacccataccteaacggatacccctacaccgaagacgacacaaaacagacctgtgaggttgtgga caaggacaaggtgtcgtgtggactttctggcatcactgctgcccaatgccaggccatcagctgctgtgtttgatgacggatgtgcttc tacgggaaaacagtgactgtccagtgtaccaaggatggccagtttgtggtggtggtttccagggatgccactctgcccaaccttga -continued gctagattccatcagcctgctaggggcaaacggagcccactgcacccctgtcggcaccacatctgcctttgccatctaccagttca aagttactgaatgtggaactgtggtgacggaggaacctgatactattgtctatgagaacaggatgtcctcttcatatgtagtgggat tggacccttcggcgacattaccagggacagccactatgacctggtcttccagtgtcggtatactgggacttccgttgagacattggtt atcgaggtgaaaacgtatccaaacccccacccagtggtcactgttgatgcagttctcaacgtggagctccgactggccaatgga cgttgtctctccaagggatgtgatgaaatgcaagaagcatacacctcttactacacggtggcagactaccctgtcaccaaggtcct cagggatcccgtgtacgctgaggttcgcatcctggggatgacagatcccaatgttgtcctgacactggagcagtgctgggccacc atagaccccacaggtgataggctgccccggtgggacctactagttaatgggtgtccctaccaggatgaccgttacctgaccgtgc ccatcgcctcggacagctcctatatccctcgggagaattcttatcccactacaagcgcttcgtcttcaagatgttcacctttgtggat ccgacatctatggtcccctgcaggagaacgtgtacatccactgtcgtgcaacagtgtgccacgctctagcaggatcctgtgaac aaaggtgcaacaggcaaaggagagatctttctgctcaaggccaaagaagactaaaggagatgttgtggtttccagtcaaaaa gtcatcatgattgacccaagtctttatgcttaa SEQ ID No. 14:
Full length nucleotide sequence encoding SEQ ID No. 6, choriogenin H - Pacific salmon
atgaagtggagtgcagtttgtctagtggcagtggccacgcttggctggctgtgtgatgctcagatttacttggaaaaaccagggtgg ccacccatccagacaccagcgtcatggcctgcccaaccccctgagaagcctgttcaaccccctcagaggcctgcccagcccc ctcagtggcctgcccagcccctcagtggcctgcccagcccctcagaggcctgcccagcccctcagaggcctgcccaaac ccagcagtggcctggccaaccccctcagaggcctgcccagcccctcagtggcctgcccaaccccctcagaggcctgcccaa cccctcaaagacctgcccaaccccctcagaggcctgcccaacccctccgaggcctgcccaaccccctcagtggcctgttcat cccctcagtggcctgtccaacccggtacgccgcttcagaggcctaaattcccctctgacccaggctcaaagcagagctgtgatg ttgatagccaacacaaggtgcagtgtggacttcctgacatcactgccgcccattgtgatgccattaactgctgttttgatggacggat gtgcttctacggaaaagcagtgactgttcagtgtaccaaggatggccagtttgtggtggtggtggcagggatgccactctgccca gcctggaactggactccatcagcctgctggggacaaacggaccccactgccatgctattggcacaacttctgtctttgccatctac cagtttaaagtcactgaatgtggaactgtcatgacggaggaaactgatactattatctatgagaataggatgtcctcttcatatcaag tgggggttggccccttggctccatcaccagggacagccaatatgatctaacattccagtgcagatataagggcagtaccattgtg gctgtggttattgatgtgaagccggttcctcctccaaatcctgatatagctcctggaccctcacagttgagctcagactcggcagcg gaacatgccttaccaagggatgtaatgaagaggaagtggcctacacctcttactacacgaggcagactaccctgtcaccaag gtcctcagggatcctgtgtacactgaggttcgcatcctggcgaggacagatcccaacattgtgctgaccctgggtcgctgctgggc taccacaaacccaaaccctctcagcctgccccagtgggaccttctcattgatggatgtccttaccaggatgaccgttacctgacca ctcccatcaatgtgggaccctcttcgggtctgtccttcccaacccactacaggcgcttcgtccttaagatgttcacctttgtggatccaa tgtctatgacccccctgagggagacggtgttcatccattgtaatacagctgtgtgtctgccatcccatggagacagctgtgaaccaa gatgctacagaaagaggagagacattcctgctgcagtccagaagaccaccagaatcaagtctaatttggtttccagtggcgaac tgatcctgactgacccaagggagctcaccaactag SEQ ID No. 15:
Full length nucleotide sequence encoding SEQ ID No. 7. choriogenin L - Pacific salmon
atggcgatgaagtggagtgtagtttgtctcgtggcagtggccatgcttggctgtctgtgttgctcagatttggccaccctccattaaa ccagtgcagcaaccttcagacccaatcgtccaccacctcagcagcctcagcaaccaccgtatcagaaacccaggatcccac caaaagaccaaacccaggccaagcagaagtttgagacaccattggattgacctatcctctggacccaaagccagagccca agattattgggggctcagaggcgagaacccctgtggctgccaattcagtgagggctgagtgcagggagaacatggtccacgtg gaagcgaagcatgacctgctggggatcggccagttgatccagctagaagacctcactttgggagactgccctatgtctggattcg acaatatcaaccaggtgctcatctttgagtctccgctgcagtcatgtggcagccagctaaggatgactaccaactccctcatctaca tcttcactctatattacaaacccaaacctctggcaaacaccccctcatcaggacaaatgacgcgatgatcaatattgagtgccac tatccaaggaaacacaatgtgagcagcctggccctgatcccaacctggacccctttctccgctgctaagtatgcagaggaactcc -continued

```
tgtacttctccatgaggctcatgactgctgactggcagtatgagagggccggtaacatgtacgtgttgggtgatatggtgaacatcg aggcctctgtcatgcagtacttccacgttcccctgcgtatctttgtggacagctgtgtggccaccctggaacccaacataaacgcca atcccagatatgccttcattgagaatcatgggtgtctgatcgatgccaaaatgacaggttcccactcccagttcatgcctcgttccgc agactacaagctgtatttccaggtggaggctttcaggttccagagccagagggggagtgacccaattattccgcagaaaacaaa gataccttttcagcctgcggcagattatcccgctacgctcgacatgatcttccttacctgtcacctgaaggcaaccacaatcgctttcc ccattgattttgagtacaaggcctgctctttcattaatacgtggagggaggctggtgggaatgatggagtgtgtggctgctgtgactc cacctgtagcaacaggaagggacgcgataccactacacatcaaaaaccagcaaatatatgggagggagatgttcagcttggt cccatctttatctcggaaaaggttgagcaataa
```

SEQ ID No. 16:
Full length Nucleotide sequence encoding SEQ ID No. 8. Altnerative zr-protein Atlantic salmon

```
gaagtggtcttaccaactccctcagaagcttgcccaaccccttcctcagaagcctgcccaacctcttcctcagtggcctgtccaac cccttcctcagaggcctgctgaacccttcctcagaggcctgctcaaccccttcctcagtggcctgtccaacccttcctcagaggc ctgctgaacccttcctcagaggcctgctcaaccccttcctcagaggcctgtccaacccttcctcagagacctgctcaaccctttct tcagaagcctgcccaacccataccctaacggatacctacaccaaagacgacacaaaacagacctgtgaggttgtggacaa ggacaaggtgtcgtgtggactttctggcatcactgctgcccaatgccaggccatcagctgctgttttgatggacggatgtgcttctac gggaaaacagtgactttccagtgtaccaaggatggccagtttgtggtggtggtttccagggatgccactctgcccaaccttgagct agattccatcagcctgctaggggcaaacggagcccactgcaccctgtcggcaccacatctgcctttgccatctaccagttcaaa gttactgaatgtggaactgtggtgacggaggaacctgatactattgtctatgagaacaggatgtcctcttcatatgtagtggggattg gacccttcggcgacattaccagggacagccactatgacctggtcttccagtgtcggtatactgggacttccgttgagacattggttat cgaggtgaaaacgtatccaaaccccaaccagtggtcactgttgatgcagttctcaacgtggagctccgactggccaatggacg ttgtctctccaagggatgtgatgaaatgcaagaagcatacacctcttactacacggtggcagactaccctgtcaccaaggtcctca gggatcccgtgtacgctgaggttcgcatcctggggatgacagatcccaatgttgtcctgacactggagcagtgctgggccaccac agaccccacaggtgataggctgccccggtgggacctactagttaatgggtgtccctaccaggatgaccgttacctgaccgtgccc atcgcctcggacagctcctatatccctcgggagaattcttatcccactacaagcgcttcgtcttcaagatgttcacctttgtggatcc gacatctatggtccccctgcaggagaacgtgtacatccactgtcgtgcaacagtgtgccacgctctagcaggatcctgtgaacaa aggtgcaacaggcaaaggagagatctttctgctcaaggccaaagaagactaaaggagatgttgtggtttccagtcaaaaagt catcatgattgacccaagtctttatgcttaa
```

The invention claimed is:

1. A pharmaceutical or cosmetic composition comprising:
   (i) an isolated polypeptide having metalloproteinase activity comprising an amino acid sequence as set forth in SEQ ID NO:1; or
   (ii) an isolated polypeptide having metalloproteinase activity comprising an amino acid sequence which is at least 90% identical to the sequence as set forth in SEQ ID NO:1; or
   (iii) an isolated polypeptide having metalloproteinase activity comprising a portion of the amino acid sequence as set forth in SEQ ID NO:1, wherein said portion comprises at least 150 amino acids; or
   (iv) an isolated polypeptide having metalloproteinase activity comprising a portion of an amino acid sequence which is at least 90% identical to a comparable region of the amino acid sequence as set forth in SEQ ID NO:1 and comprises at least 150 amino acids; and/or
   (v) one or more isolated nucleic acid molecules encoding a polypeptide as set forth in any of (i) to (iv) above or a sequence fully complementary thereof,
   an effective amount of an added stabilizing agent wherein the stabilizing agent stabilizes the isolated polypeptide having metalloproteinase activity or the isolated one or more nucleic acid molecules against degradation, and
   one or more pharmaceutically or cosmetically acceptable excipients and/or diluents, wherein the composition is a gel, cream, ointment, lotion, foam, non-aqueous solution, spray, salve, stick, soap, powder, film, emulsion, suspension or dispersion.

2. A composition as claimed in claim 1 wherein said nucleic acid molecule of (v) comprises:
   (a) a nucleotide sequence as set forth in SEQ ID NO:9; or
   (b) a nucleotide sequence which is at least 90% identical to the sequence as set forth in SEQ ID NO:9; or
   (c) a portion of the nucleotide sequence as set forth in SEQ ID NO:9, wherein said portion comprises at least 450 nucleotide bases; or
   (d) a portion of a nucleotide sequence which is at least 90% identical to a comparable region of the sequence as set forth in SEQ ID NO:9 and comprises at least 450 nucleotide bases; or
   (e) a nucleotide sequence which hybridizes to the sequence as set forth in SEQ ID NO:9 under non-stringent binding conditions of 6×SSC/50% formamide at room temperature and washing under conditions of high stringency; or
   (f) a nucleotide sequence fully complementary to any of the aforesaid sequences.

3. A composition as claimed in claim 1, wherein said amino acid sequence is at least 95% identical to the amino acid sequence as set forth in SEQ ID NO:1.

4. A composition as claimed in claim 1, wherein said portion is at least 95% identical to a comparable region of the amino acid sequence as set forth in SEQ ID NO:1.

5. A composition as claimed in claim 1, wherein said composition is a gel, cream, ointment or lotion.

6. A composition as claimed in claim 1, wherein said composition is for topical administration.

7. A composition as claimed in claim 1, wherein the polypeptide is in the concentration range of 0.0001-25% [w/w].

8. A composition as claimed in claim 1, wherein the polypeptide is in the concentration range of 0.005-15% [w/w].

9. A composition as claimed in claim 1, wherein the stabilizing agent is Tris, phosphate or acetate buffer.

10. A cosmetic or non-cosmetic method of exfoliating and/or moisturizing skin of an animal, wherein an effective amount of a cosmetic or a pharmaceutical composition is topically administered to said animal, wherein said cosmetic or pharmaceutical composition comprises:
   (i) an isolated polypeptide having metalloproteinase activity comprising an amino acid sequence as set forth in SEQ ID NO:1; or
   (ii) an isolated polypeptide having metalloproteinase activity comprising an amino acid sequence which is at least 90% identical to a sequence as set forth in SEQ ID NO: 1; or
   (iii) an isolated polypeptide having metalloproteinase activity comprising a portion of an amino acid sequence as set forth in SEQ ID NO: 1, wherein said portion comprises at least 150 amino acids; or
   (iv) an isolated polypeptide having metalloproteinase activity comprising a portion of an amino acid sequence which is at least 90% identical to a comparable region of an amino acid sequence as set forth in SEQ ID NO: 1 and comprises at least 150 amino acids; and/or
   (v) one or more isolated nucleic acid molecules encoding a polypeptide as set forth in any of (i) to (iv) above or a sequence fully complementary thereof,
   and one or more pharmaceutically or cosmetically acceptable excipients and/or diluents.

11. A method as claimed in claim 10, wherein the composition is administered to said animal at a dose of 0.1-100mU/cm$^2$/day.

12. A method a claimed in claim 10, wherein said isolated nucleic acid molecule of (v) comprises:
   (a) a nucleotide sequence as set forth in SEQ ID NO: 9; or
   (b) a nucleotide sequence which is at least 90% identical to a sequence as set forth in SEQ ID NO: 9; or
   (c) a portion of a nucleotide sequence as set forth in SEQ ID NO: 9, wherein said portion comprises at least 450 nucleotide bases; or
   (d) a portion of a nucleotide sequence which is at least 90% identical to a comparable region of a sequence as set forth in SEQ ID NO: 9 and comprises at least 450 nucleotide bases; or
   (e) a nucleotide sequence which hybridizes to a sequence as set forth in SEQ ID NO: 9 under non-stringent binding conditions of 6×SSC/50% formamide at room temperature and washing under conditions of high stringency; or
   (f) a nucleotide sequence fully complementary to any of the aforesaid sequences.

13. A method as claimed in claim 10, wherein said amino acid sequence is at least 95% identical to an amino acid sequence as set forth in SEQ ID NO: 1.

14. A method as claimed in claim 10, wherein said portion is at least 95% identical to a comparable region of an amino acid sequence as set forth in SEQ ID NO: 1.

15. A method as claimed in claim 10, wherein said composition is a gel, cream, ointment or lotion.

16. A method as claimed in claim 10, wherein the polypeptide is in the concentration range of 0.0001-25% [w/w].

17. A method as claimed in claim 10, wherein the polypeptide is in the concentration range of 0.005-15% [w/w].

\* \* \* \* \*

SEQUENCE LISTING

<160> NUMBER OF SEQ ID NOS: 46

<210> SEQ ID NO 1
<211> LENGTH: 262
<212> TYPE: PRT
<213> ORGANISM: Salmo salar

<400> SEQUENCE: 1

Met Asp His Arg Pro Thr Leu Ser Leu Leu Leu Leu Leu Leu Leu Leu
1               5                   10                  15

Gly Leu Ser Gln Ala Ser Gly Asn Glu Phe His Asp Glu Pro Asp His
            20                  25                  30

Val Ser Ile Thr Ser Val Ile Leu Lys Ser Asn Asn Gly Thr Asn Glu
        35                  40                  45

Leu Leu Leu Asp Gly Asp Ile Leu Ala Pro Arg Thr Arg Asn Ala Met
    50                  55                  60

Lys Cys Phe Ser Ser Gln Tyr Ser Cys Leu Trp Lys Lys Ser Ser Asp

```
                65                  70                  75                  80
        Gly Leu Val Tyr Val Pro Tyr Ile Leu Ser Ala Val Tyr Ser Ser Leu
                        85                  90                  95

Glu Val Glu Thr Ile Glu Thr Ala Met Lys Tyr Phe Gln Gly Lys Thr
                        100                 105                 110

Cys Ile Arg Phe Ile Pro Arg Lys Thr Gln Thr Ala Tyr Leu Asp Ile
                        115                 120                 125

Gln Ser Ser Gly Gly Cys Phe Gly Thr Val Gly Thr Val Gly Asp Arg
                    130                 135                 140

Gln Thr Leu Ser Leu Ala Gln Phe Gly Cys Val Gln His Gly Ile Ile
        145                 150                 155                 160

Gln His Glu Leu Leu His Ala Leu Gly Phe Tyr His Glu His Asn Arg
                        165                 170                 175

Ser Asp Arg Glu Gln Tyr Ile Arg Ile Asn Trp Gln Tyr Ile Tyr Asp
                        180                 185                 190

Tyr Ala Val Gly Asn Phe Gln Lys Glu Asp Thr Asn Asn Leu His Thr
                        195                 200                 205

Ala Tyr Asp Tyr Ser Ser Val Met His Tyr Arg Thr Ala Tyr Thr
                    210                 215                 220

Asn Asp Tyr Gly Lys Glu Thr Ile Thr Pro Ile Pro Asp Pro Ser Val
        225                 230                 235                 240

Ala Ile Gly Gln Arg Leu Gly Met Ser Asp Ile Asp Val Leu Lys Val
                        245                 250                 255

Asn Lys Leu Tyr Gln Cys
                        260

<210> SEQ ID NO 2
<211> LENGTH: 117
<212> TYPE: PRT
<213> ORGANISM: Salmo salar

<400> SEQUENCE: 2

Thr Val Thr Val Gln Cys Thr Lys Asp Gly Gln Phe Val Val Val
1               5                   10                  15

Ser Arg Asp Ala Thr Leu Pro Asn Leu Glu Leu Asp Ser Ile Ser Leu
                20                  25                  30

Leu Gly Ala Asn Gly Ala His Cys Thr Pro Val Gly Thr Thr Ser Ala
            35                  40                  45

Phe Ala Ile Tyr Gln Phe Lys Val Thr Glu Cys Gly Thr Val Val Thr
    50                  55                  60

Glu Glu Pro Asp Thr Ile Val Tyr Glu Asn Arg Met Ser Ser Ser Tyr
65                  70                  75                  80

Val Val Gly Ile Gly Pro Phe Gly Asp Ile Thr Arg Asp Ser His Tyr
                85                  90                  95

Asp Leu Val Phe Gln Cys Arg Tyr Thr Gly Thr Ser Val Glu Thr Leu
                100                 105                 110

Val Ile Glu Val Lys
            115

<210> SEQ ID NO 3
<211> LENGTH: 261
<212> TYPE: PRT
<213> ORGANISM: Salmo salar

<400> SEQUENCE: 3

Ala Val Thr Val Gln Cys Thr Lys Asp Gly Gln Phe Val Val Val Val
```

```
              1               5                  10                 15
            Ala Arg Asp Ala Thr Leu Pro Ser Leu Glu Leu Asp Ser Ile Ser Leu
                            20                 25                 30

Leu Gly Thr Asn Gly Pro His Cys His Ala Ile Gly Thr Thr Ser Val
                            35                 40                 45

Phe Ala Ile Tyr Gln Phe Lys Val Thr Glu Cys Gly Thr Val Met Thr
                50                 55                 60

Glu Glu Thr Asp Thr Ile Ile Tyr Glu Asn Arg Met Ser Ser Ser Tyr
             65                 70                 75                 80

Gln Val Gly Val Gly Pro Phe Gly Ser Ile Thr Arg Asp Ser Gln Tyr
                            85                 90                 95

Asp Leu Thr Phe Gln Cys Arg Tyr Lys Gly Ser Thr Ile Val Ala Val
                            100                105                110

Val Ile Asp Val Lys Pro Val Pro Pro Asn Pro Asp Ile Ala Pro
                            115                120                125

Gly Pro Leu Thr Val Glu Leu Arg Leu Gly Ser Gly Thr Cys Leu Thr
                            130                135                140

Lys Gly Cys Asn Glu Glu Val Ala Tyr Thr Ser Tyr Tyr Thr Glu
            145                150                155                160

Ala Asp Tyr Pro Val Thr Lys Val Leu Arg Asp Pro Val Tyr Thr Glu
                            165                170                175

Val Arg Ile Leu Ala Arg Thr Asp Pro Asn Ile Val Leu Thr Leu Gly
                            180                185                190

Arg Cys Trp Ala Thr Thr Asn Pro Asn Pro Leu Ser Leu Pro Gln Trp
                            195                200                205

Asp Leu Leu Ile Asp Gly Cys Pro Tyr Gln Asp Asp Arg Tyr Leu Thr
                            210                215                220

Thr Pro Ile Asn Val Gly Pro Ser Ser Gly Leu Ser Phe Pro Thr His
            225                230                235                240

Tyr Arg Arg Phe Val Leu Lys Met Phe Thr Phe Val Asp Pro Met Ser
                            245                250                255

Met Thr Pro Leu Arg
                            260

<210> SEQ ID NO 4
<211> LENGTH: 224
<212> TYPE: PRT
<213> ORGANISM: Salmo salar

<400> SEQUENCE: 4

Ala Glu Cys Arg Glu Asn Met Val His Val Glu Ala Lys His Asp Leu
             1                 5                  10                 15

Leu Gly Ile Gly Gln Leu Ile Gln Leu Glu Asp Leu Thr Leu Gly Asp
                            20                 25                 30

Cys Pro Met Ser Gly Phe Asp Asn Ile Asn Gln Val Leu Ile Phe Glu
                            35                 40                 45

Ser Pro Leu Gln Ser Cys Gly Ser Gln Leu Arg Met Thr Thr Asn Ser
                50                 55                 60

Leu Ile Tyr Ile Phe Thr Leu Tyr Tyr Lys Pro Lys Pro Leu Ala Asn
             65                 70                 75                 80

Thr Pro Leu Ile Arg Thr Asn Asp Ala Met Ile Asn Ile Glu Cys His
                            85                 90                 95

Tyr Pro Arg Lys His Asn Val Ser Ser Leu Ala Leu Ile Pro Thr Trp
                            100                105                110
```

```
Thr Pro Phe Ser Ala Ala Lys Tyr Ala Glu Glu Leu Leu Tyr Phe Ser
        115                 120                 125

Met Arg Leu Met Thr Ala Asp Trp Gln Tyr Glu Arg Ala Gly Asn Met
130                 135                 140

Tyr Val Leu Gly Asp Met Val Asn Ile Glu Ala Ser Val Met Gln Tyr
145                 150                 155                 160

Phe His Val Pro Leu Arg Ile Phe Val Asp Ser Cys Val Ala Thr Leu
                165                 170                 175

Glu Pro Asn Ile Asn Ala Asn Pro Arg Tyr Ala Phe Ile Glu Asn His
                180                 185                 190

Gly Cys Leu Ile Asp Ala Lys Met Thr Gly Ser His Ser Gln Phe Met
            195                 200                 205

Pro Arg Ser Ala Asp Tyr Lys Leu Tyr Phe Gln Val Glu Ala Phe Arg
    210                 215                 220
```

<210> SEQ ID NO 5
<211> LENGTH: 439
<212> TYPE: PRT
<213> ORGANISM: Salmo salar

<400> SEQUENCE: 5

```
Met Lys Trp Ser Ala Val Cys Leu Val Ala Val Ala Thr Leu Gly Trp
1               5                   10                  15

Leu Cys Asp Ala Gln Asn Phe Leu Glu Lys Pro Gly Trp Pro Pro Ile
            20                  25                  30

Gln Thr Pro Pro Ser Trp Pro Pro Gln Thr Pro Gln Arg Pro Val Gln
        35                  40                  45

Pro Leu Pro Gln Arg Pro Ala Gln Pro Phe Leu Gln Lys Pro Ala Gln
50                  55                  60

Pro Ile Pro Gln Arg Ile Pro Tyr Thr Glu Asp Thr Lys Gln Thr
65                  70                  75                  80

Cys Glu Val Val Asp Lys Asp Lys Val Ser Cys Gly Leu Ser Gly Ile
                85                  90                  95

Thr Ala Ala Gln Cys Gln Ala Ile Ser Cys Cys Phe Asp Gly Arg Met
            100                 105                 110

Cys Phe Tyr Gly Lys Thr Val Thr Val Gln Cys Thr Lys Asp Gly Gln
        115                 120                 125

Phe Val Val Val Ser Arg Asp Ala Thr Leu Pro Asn Leu Glu Leu
    130                 135                 140

Asp Ser Ile Ser Leu Leu Gly Ala Asn Gly Ala His Cys Thr Pro Val
145                 150                 155                 160

Gly Thr Thr Ser Ala Phe Ala Ile Tyr Gln Phe Lys Val Thr Glu Cys
                165                 170                 175

Gly Thr Val Val Thr Glu Glu Pro Asp Thr Ile Val Tyr Glu Asn Arg
            180                 185                 190

Met Ser Ser Ser Tyr Val Val Gly Ile Gly Pro Phe Gly Asp Ile Thr
        195                 200                 205

Arg Asp Ser His Tyr Asp Leu Val Phe Gln Cys Arg Tyr Thr Gly Thr
    210                 215                 220

Ser Val Glu Thr Leu Val Ile Glu Val Lys Thr Tyr Pro Asn Pro Asn
225                 230                 235                 240

Pro Val Val Thr Val Asp Ala Val Leu Asn Val Glu Leu Arg Leu Ala
                245                 250                 255

Asn Gly Arg Cys Leu Ser Lys Gly Cys Asp Glu Met Gln Glu Ala Tyr
            260                 265                 270
```

```
Thr Ser Tyr Tyr Thr Val Ala Asp Tyr Pro Val Thr Lys Val Leu Arg
        275                 280                 285

Asp Pro Val Tyr Ala Glu Val Arg Ile Leu Gly Met Thr Asp Pro Asn
290                 295                 300

Val Val Leu Thr Leu Glu Gln Cys Trp Ala Thr Ile Asp Pro Thr Gly
305                 310                 315                 320

Asp Arg Leu Pro Arg Trp Asp Leu Leu Val Asn Gly Cys Pro Tyr Gln
                325                 330                 335

Asp Asp Arg Tyr Leu Thr Val Pro Ile Ala Ser Asp Ser Ser Tyr Ile
                340                 345                 350

Pro Pro Gly Glu Phe Leu Ser His Tyr Lys Arg Phe Val Phe Lys Met
            355                 360                 365

Phe Thr Phe Val Asp Pro Thr Ser Met Val Pro Leu Gln Glu Asn Val
        370                 375                 380

Tyr Ile His Cys Arg Ala Thr Val Cys His Ala Leu Ala Gly Ser Cys
385                 390                 395                 400

Glu Gln Arg Cys Asn Arg Gln Arg Arg Asp Leu Ser Ala Gln Gly Gln
                405                 410                 415

Lys Lys Thr Lys Gly Asp Val Val Ser Ser Gln Lys Val Ile Met
            420                 425                 430

Ile Asp Pro Ser Leu Tyr Ala
            435

<210> SEQ ID NO 6
<211> LENGTH: 524
<212> TYPE: PRT
<213> ORGANISM: Oncorhynchus masou

<400> SEQUENCE: 6

Met Lys Trp Ser Ala Val Cys Leu Val Ala Val Ala Thr Leu Gly Trp
1               5                   10                  15

Leu Cys Asp Ala Gln Ile Tyr Leu Glu Lys Pro Gly Trp Pro Pro Ile
            20                  25                  30

Gln Thr Pro Ala Ser Trp Pro Ala Gln Pro Glu Lys Pro Val Gln
        35                  40                  45

Pro Pro Gln Arg Pro Ala Gln Pro Pro Gln Trp Pro Ala Gln Pro Pro
    50                  55                  60

Gln Trp Pro Ala Gln Pro Gln Arg Pro Ala Gln Pro Gln Arg
65                  70                  75                  80

Pro Ala Gln Thr Gln Gln Trp Pro Gly Gln Pro Gln Arg Pro Ala
                85                  90                  95

Gln Pro Pro Gln Trp Pro Ala Gln Pro Pro Gln Arg Pro Ala Gln Pro
            100                 105                 110

Pro Gln Arg Pro Ala Gln Pro Gln Arg Pro Ala Gln Pro Pro Pro
        115                 120                 125

Arg Pro Ala Gln Pro Pro Gln Trp Pro Val His Pro Gln Trp Pro
130                 135                 140

Val Gln Pro Gly Thr Pro Leu Gln Arg Pro Lys Phe Pro Ser Asp Pro
145                 150                 155                 160

Gly Ser Lys Gln Ser Cys Asp Val Asp Ser Gln His Lys Val Gln Cys
                165                 170                 175

Gly Leu Pro Asp Ile Thr Ala Ala His Cys Asp Ala Ile Asn Cys Cys
            180                 185                 190

Phe Asp Gly Arg Met Cys Phe Tyr Gly Lys Ala Val Thr Val Gln Cys
```

```
                195                 200                 205
Thr Lys Asp Gly Gln Phe Val Val Val Ala Arg Asp Ala Thr Leu
    210                 215                 220

Pro Ser Leu Glu Leu Asp Ser Ile Ser Leu Leu Gly Thr Asn Gly Pro
225                 230                 235                 240

His Cys His Ala Ile Gly Thr Thr Ser Val Phe Ala Ile Tyr Gln Phe
                245                 250                 255

Lys Val Thr Glu Cys Gly Thr Val Met Thr Glu Glu Thr Asp Thr Ile
            260                 265                 270

Ile Tyr Glu Asn Arg Met Ser Ser Tyr Gln Val Gly Val Gly Pro
        275                 280                 285

Phe Gly Ser Ile Thr Arg Asp Ser Gln Tyr Asp Leu Thr Phe Gln Cys
290                 295                 300

Arg Tyr Lys Gly Ser Thr Ile Val Ala Val Ile Asp Val Lys Pro
305                 310                 315                 320

Val Pro Pro Asn Pro Asp Ile Ala Pro Gly Pro Leu Thr Val Glu
                325                 330                 335

Leu Arg Leu Gly Ser Gly Thr Cys Leu Thr Lys Gly Cys Asn Glu Glu
            340                 345                 350

Glu Val Ala Tyr Thr Ser Tyr Tyr Thr Glu Ala Asp Tyr Pro Val Thr
        355                 360                 365

Lys Val Leu Arg Asp Pro Val Tyr Thr Glu Val Arg Ile Leu Ala Arg
    370                 375                 380

Thr Asp Pro Asn Ile Val Leu Thr Leu Gly Arg Cys Trp Ala Thr Thr
385                 390                 395                 400

Asn Pro Asn Pro Leu Ser Leu Pro Gln Trp Asp Leu Leu Ile Asp Gly
                405                 410                 415

Cys Pro Tyr Gln Asp Asp Arg Tyr Leu Thr Thr Pro Ile Asn Val Gly
            420                 425                 430

Pro Ser Ser Gly Leu Ser Phe Pro Thr His Tyr Arg Arg Phe Val Leu
        435                 440                 445

Lys Met Phe Thr Phe Val Asp Pro Met Ser Met Thr Pro Leu Arg Glu
    450                 455                 460

Thr Val Phe Ile His Cys Asn Thr Ala Val Cys Leu Pro Ser His Gly
465                 470                 475                 480

Asp Ser Cys Glu Pro Arg Cys Tyr Arg Lys Arg Asp Ile Pro Ala
                485                 490                 495

Ala Val Gln Lys Thr Thr Arg Ile Lys Ser Asn Leu Val Ser Ser Gly
            500                 505                 510

Glu Leu Ile Leu Thr Asp Pro Arg Glu Leu Thr Asn
        515                 520

<210> SEQ ID NO 7
<211> LENGTH: 438
<212> TYPE: PRT
<213> ORGANISM: Oncorhynchus masou

<400> SEQUENCE: 7

Met Ala Met Lys Trp Ser Val Val Cys Leu Val Ala Val Ala Met Leu
1               5                   10                  15

Gly Cys Leu Cys Val Ala Gln Ile Trp Pro Ser Ile Lys Pro Val
            20                  25                  30

Gln Gln Pro Phe Arg Pro Asn Arg Pro Pro Gln Gln Pro Gln Gln
        35                  40                  45
```

```
Pro Pro Tyr Gln Lys Pro Arg Ile Pro Pro Lys Asp Gln Thr Gln Ala
         50                   55                  60
Lys Gln Lys Phe Glu Thr Pro Leu Asp Trp Thr Tyr Pro Leu Asp Pro
 65                  70                  75                  80
Lys Pro Glu Pro Lys Ile Ile Gly Gly Ser Glu Ala Arg Thr Pro Val
                 85                  90                  95
Ala Ala Asn Ser Val Arg Ala Glu Cys Arg Glu Asn Met Val His Val
             100                 105                 110
Glu Ala Lys His Asp Leu Leu Gly Ile Gly Gln Leu Ile Gln Leu Glu
             115                 120                 125
Asp Leu Thr Leu Gly Asp Cys Pro Met Ser Gly Phe Asp Asn Ile Asn
130                 135                 140
Gln Val Leu Ile Phe Glu Ser Pro Leu Gln Ser Cys Gly Ser Gln Leu
145                 150                 155                 160
Arg Met Thr Thr Asn Ser Leu Ile Tyr Ile Phe Thr Leu Tyr Tyr Lys
                165                 170                 175
Pro Lys Pro Leu Ala Asn Thr Pro Leu Ile Arg Thr Asn Asp Ala Met
                180                 185                 190
Ile Asn Ile Glu Cys His Tyr Pro Arg Lys His Asn Val Ser Ser Leu
            195                 200                 205
Ala Leu Ile Pro Thr Trp Thr Pro Phe Ser Ala Ala Lys Tyr Ala Glu
210                 215                 220
Glu Leu Leu Tyr Phe Ser Met Arg Leu Met Thr Ala Asp Trp Gln Tyr
225                 230                 235                 240
Glu Arg Ala Gly Asn Met Tyr Val Leu Gly Asp Met Val Asn Ile Glu
                245                 250                 255
Ala Ser Val Met Gln Tyr Phe His Val Pro Leu Arg Ile Phe Val Asp
            260                 265                 270
Ser Cys Val Ala Thr Leu Glu Pro Asn Ile Asn Ala Asn Pro Arg Tyr
        275                 280                 285
Ala Phe Ile Glu Asn His Gly Cys Leu Ile Asp Ala Lys Met Thr Gly
290                 295                 300
Ser His Ser Gln Phe Met Pro Arg Ser Ala Asp Tyr Lys Leu Tyr Phe
305                 310                 315                 320
Gln Val Glu Ala Phe Arg Phe Gln Ser Gln Arg Gly Ser Asp Pro Ile
                325                 330                 335
Ile Pro Gln Lys Thr Lys Ile Pro Phe Gln Pro Ala Ala Asp Tyr Pro
                340                 345                 350
Ala Thr Leu Asp Met Ile Phe Leu Thr Cys His Leu Lys Ala Thr Thr
            355                 360                 365
Ile Ala Phe Pro Ile Asp Phe Glu Tyr Lys Ala Cys Ser Phe Ile Asn
370                 375                 380
Thr Trp Arg Glu Ala Gly Gly Asn Asp Gly Val Cys Gly Cys Cys Asp
385                 390                 395                 400
Ser Thr Cys Ser Asn Arg Lys Gly Arg Asp Thr Thr Thr His Gln Lys
                405                 410                 415
Pro Ala Asn Ile Trp Glu Gly Asp Val Gln Leu Gly Pro Ile Phe Ile
                420                 425                 430
Ser Glu Lys Val Glu Gln
                435

<210> SEQ ID NO 8
<211> LENGTH: 467
<212> TYPE: PRT
```

<213> ORGANISM: Salmo salar

<400> SEQUENCE: 8

```
Lys Trp Ser Tyr Gln Leu Pro Gln Lys Leu Ala Gln Pro Leu Pro Gln
1               5                   10                  15
Lys Pro Ala Gln Pro Leu Pro Gln Trp Pro Val Gln Pro Leu Pro Gln
            20                  25                  30
Arg Pro Ala Glu Pro Leu Pro Gln Arg Pro Ala Gln Pro Leu Pro Gln
        35                  40                  45
Trp Pro Val Gln Pro Leu Pro Gln Arg Pro Ala Glu Pro Leu Pro Gln
    50                  55                  60
Arg Pro Ala Gln Pro Leu Pro Gln Arg Pro Val Gln Pro Leu Pro Gln
65                  70                  75                  80
Arg Pro Ala Gln Pro Phe Leu Gln Lys Pro Ala Gln Pro Ile Pro Gln
                85                  90                  95
Arg Ile Pro Tyr Thr Lys Asp Asp Thr Lys Gln Thr Cys Glu Val Val
            100                 105                 110
Asp Lys Asp Lys Val Ser Cys Gly Leu Ser Gly Ile Thr Ala Ala Gln
        115                 120                 125
Cys Gln Ala Ile Ser Cys Cys Phe Asp Gly Arg Met Cys Phe Tyr Gly
    130                 135                 140
Lys Thr Val Thr Phe Gln Cys Thr Lys Asp Gly Gln Phe Val Val Val
145                 150                 155                 160
Val Ser Arg Asp Ala Thr Leu Pro Asn Leu Glu Leu Asp Ser Ile Ser
                165                 170                 175
Leu Leu Gly Ala Asn Gly Ala His Cys Thr Pro Val Gly Thr Thr Ser
            180                 185                 190
Ala Phe Ala Ile Tyr Gln Phe Lys Val Thr Glu Cys Gly Thr Val Val
        195                 200                 205
Thr Glu Glu Pro Asp Thr Ile Val Tyr Glu Asn Arg Met Ser Ser Ser
    210                 215                 220
Tyr Val Val Gly Ile Gly Pro Phe Gly Asp Ile Thr Arg Asp Ser His
225                 230                 235                 240
Tyr Asp Leu Val Phe Gln Cys Arg Tyr Thr Gly Thr Ser Val Glu Thr
                245                 250                 255
Leu Val Ile Glu Val Lys Thr Tyr Pro Asn Pro Asn Pro Val Val Thr
            260                 265                 270
Val Asp Ala Val Leu Asn Val Glu Leu Arg Leu Ala Asn Gly Arg Cys
        275                 280                 285
Leu Ser Lys Gly Cys Asp Glu Met Gln Glu Ala Tyr Thr Ser Tyr Tyr
    290                 295                 300
Thr Val Ala Asp Tyr Pro Val Thr Lys Val Leu Arg Asp Pro Val Tyr
305                 310                 315                 320
Ala Glu Val Arg Ile Leu Gly Met Thr Asp Pro Asn Val Val Leu Thr
                325                 330                 335
Leu Glu Gln Cys Trp Ala Thr Thr Asp Pro Thr Gly Asp Arg Leu Pro
            340                 345                 350
Arg Trp Asp Leu Leu Val Asn Gly Cys Pro Tyr Gln Asp Asp Arg Tyr
        355                 360                 365
Leu Thr Val Pro Ile Ala Ser Asp Ser Ser Tyr Ile Pro Pro Gly Glu
    370                 375                 380
Phe Leu Ser His Tyr Lys Arg Phe Val Phe Lys Met Phe Thr Phe Val
385                 390                 395                 400
```

```
Asp Pro Thr Ser Met Val Pro Leu Gln Glu Asn Val Tyr Ile His Cys
            405                 410                 415

Arg Ala Thr Val Cys His Ala Leu Ala Gly Ser Cys Glu Gln Arg Cys
        420                 425                 430

Asn Arg Gln Arg Arg Asp Leu Ser Ala Gln Gly Gln Lys Lys Thr Lys
            435                 440                 445

Gly Asp Val Val Ser Ser Gln Lys Val Ile Met Ile Asp Pro Ser
    450                 455                 460

Leu Tyr Ala
465

<210> SEQ ID NO 9
<211> LENGTH: 924
<212> TYPE: DNA
<213> ORGANISM: Salmo salar

<400> SEQUENCE: 9
atggaccaca gacccactct tagcctgctt ctgctgctgc tgctgctggg cctatcacag     60
gccagtggaa atgagttcca tgatgagccg accatgtgt ccatcacttc agtaatcctg    120
aagtccaaca acgaaccaa tgagctactg ctggatggag acattctagc tcctagaacc    180
aggaacgcca tgaagtgctt tagcagccag tacagctgtc tctggaagaa gtcatctgac    240
ggcttggtgt acgtgcctta catcctcagc gctgtatatt ccagcttgga ggtagagact    300
attgagacgg ccatgaagta cttccaaggc aagacctgca tccgcttcat tccacgtaag    360
acacagactg cctacctgga cattcagagc agcggcgggt gttttggtac cgtggggact    420
gttggggaca ggcagacatt gtctcttgca cagtttggct gtgttcaaca tggtatcatc    480
cagcatgagc tgcttcacgc cctgggcttc taccacgagc acaacaggag tgaccgtgaa    540
cagtatatca ggatcaactg caatacatc tatgactacg ccgttgggaa cttccagaag    600
gaggacacca caaacctgca cactgcatac gactactcct ctgtcatgca ctatgataga    660
accgcttaca ctaacgacta cggaaaggaa accatcactc ccatcccaga cccatctgtg    720
gccattggac agagactggg catgtccgac attgatgtcc tgaaggtcaa caagctctac    780
caatgctaag aggaagagcg ccattgttga aaatgtgtga tgctggatgt gctgtcatgt    840
gctgatgtat tttattgttg gaagtttgta tgtatccttt taatcacatt ggtaataata    900
aagcatggtt atggtaaaaa aaaa                                            924

<210> SEQ ID NO 10
<211> LENGTH: 351
<212> TYPE: DNA
<213> ORGANISM: Salmo salar

<400> SEQUENCE: 10
acagtgactg tccagtgtac caaggatggc cagtttgtgg tggtggtttc cagggatgcc     60
actctgccca accttgagct agattccatc agcctgctag ggcaaacgg agcccactgc    120 accctgtcg gcaccacatc tgcctttgcc atctaccagt tcaaagttac tgaatgtgga    180
actgtggtga cggaggaacc tgatactatt gtctatgaga acaggatgtc ctcttcatat    240
gtagtgggga ttggaccctt cggcgacatt accaggaca gccactatga cctggtcttc    300
cagtgtcggt atactgggac ttccgttgag acattggtta tcgaggtgaa a            351

<210> SEQ ID NO 11
<211> LENGTH: 783
<212> TYPE: DNA
```

<213> ORGANISM: Salmo salar

<400> SEQUENCE: 11

```
gcagtgactg ttcagtgtac caaggatggc cagtttgtgg tggtggtggc cagggatgcc      60
actctgccca gcctggaact ggactccatc agcctgctgg ggacaaacgg accccactgc     120
catgctattg gcacaacttc tgtctttgcc atctaccagt ttaaagtcac tgaatgtgga     180
actgtcatga cggaggaaac tgatactatt atctatgaga ataggatgtc ctcttcatat     240
caagtggggg ttggcccctt tggctccatc accagggaca gccaatatga tctaacattc     300
cagtgcagat ataagggcag taccattgtg gctgtggtta ttgatgtgaa gccggttcct     360
cctccaaatc ctgatatagc tcctggaccc ctcacagttg agctcagact cggcagcgga     420
acatgcctta ccaagggatg taatgaagag gaagtggcct acacctctta ctacacagag     480
gcagactacc ctgtcaccaa ggtcctcagg gatcctgtgt acactgaggt tcgcatcctg     540
gcgaggacag atcccaacat tgtgctgacc ctgggtcgct gctgggctac cacaaaccca     600
aaccctctca gcctgcccca gtgggacctt ctcattgatg gatgtcctta ccaggatgac     660
cgttacctga ccactcccat caatgtggga ccctcttcgg gtctgtcctt cccaacccac     720
tacaggcgct tcgtccttaa gatgttcacc tttgtggatc caatgtctat gaccccctg     780
agg                                                                   783
```

<210> SEQ ID NO 12
<211> LENGTH: 672
<212> TYPE: DNA
<213> ORGANISM: Salmo salar

<400> SEQUENCE: 12

```
gctgagtgca gggagaacat ggtccacgtg gaagcgaagc atgacctgct ggggatcggc      60
cagttgatcc agctagaaga cctcactttg ggagactgcc ctatgtctgg attcgacaat     120
atcaaccagg tgctcatctt tgagtctccg ctgcagtcat gtggcagcca gctaaggatg     180
actaccaact ccctcatcta catcttcact ctatattaca aacccaaacc tctggcaaac     240
accccctca tcaggacaaa tgacgcgatg atcaatattg agtgccacta tccaaggaaa     300
cacaatgtga gcagcctggc cctgatccca acctggaccc ctttctccgc tgctaagtat     360
gcagaggaac tcctgtactt ctccatgagg ctcatgactg ctgactggca gtatgagagg     420
gccggtaaca tgtacgtgtt gggtgatatg gtgaacatcg aggcctctgt catgcagtac     480
ttccacgttc ccctgcgtat ctttgtggac agctgtgtgg ccaccctgga acccaacata     540
aacgccaatc ccagatatgc cttcattgag aatcatgggt gtctgatcga tgccaaaatg     600
acaggttccc actcccagtt catgcctcgt tccgcagact caagctgta tttccaggtg     660
gaggctttca gg                                                         672
```

<210> SEQ ID NO 13
<211> LENGTH: 1320
<212> TYPE: DNA
<213> ORGANISM: Salmo salar

<400> SEQUENCE: 13

```
atgaagtgga gtgcagtttg tctagtggca gtggccacgc ttggctggct gtgtgatgct      60
cagaatttct tggaaaaacc agggtggcca cccatccaga caccaccgtc atggcctccc     120
caaaccctc agaggcctgt ccaacccctt cctcagagac tgctcaacc cttcttcag      180
aagcctgccc aacccatacc tcaacggata ccctacaccg aagacgacac aaaacagacc     240
```

| | |
|---|---|
| tgtgaggttg tggacaagga caaggtgtcg tgtggacttt ctggcatcac tgctgcccaa | 300 |
| tgccaggcca tcagctgctg ttttgatgga cggatgtgct tctacgggaa aacagtgact | 360 |
| gtccagtgta ccaaggatgg ccagtttgtg gtggtggttt ccagggatgc cactctgccc | 420 |
| aaccttgagc tagattccat cagcctgcta ggggcaaacg gagcccactg caccccctgtc | 480 |
| ggcaccacat ctgcctttgc catctaccag ttcaaagtta ctgaatgtgg aactgtggtg | 540 |
| acggaggaac ctgatactat tgtctatgag aacaggatgt cctcttcata tgtagtgggg | 600 |
| attggaccct tcggcgacat taccagggac agccactatg acctggtctt ccagtgtcgg | 660 |
| tatactggga cttccgttga cattggtt atcgaggtga aaacgtatcc aaaccccaac | 720 |
| ccagtggtca ctgttgatgc agttctcaac gtggagctcc gactggccaa tggacgttgt | 780 |
| ctctccaagg gatgtgatga atgcaagaa gcatacacct cttactacac ggtggcagac | 840 |
| taccctgtca ccaaggtcct cagggatccc gtgtacgctg aggttcgcat cctggggatg | 900 |
| acagatccca tgttgtcct gacactggag cagtgctggg ccaccataga ccccacaggt | 960 |
| gataggctgc cccggtggga cctactagtt aatgggtgtc cctaccagga tgaccgttac | 1020 |
| ctgaccgtgc ccatcgcctc ggacagctcc tatatccctc cgggagaatt cttatcccac | 1080 |
| tacaagcgct tcgtcttcaa gatgttcacc tttgtggatc cgacatctat ggtcccctg | 1140 |
| caggagaacg tgtacatcca ctgtcgtgca acagtgtgcc acgctctagc aggatcctgt | 1200 |
| gaacaaaggt gcaacaggca aggagagat ctttctgctc aaggccaaaa gaagactaaa | 1260 |
| ggagatgttg tggtttccag tcaaaaagtc atcatgattg acccaagtct ttatgcttaa | 1320 |

<210> SEQ ID NO 14
<211> LENGTH: 1575
<212> TYPE: DNA
<213> ORGANISM: Oncorhynchus masou

<400> SEQUENCE: 14

| | |
|---|---|
| atgaagtgga gtgcagtttg tctagtggca gtggccacgc ttggctggct gtgtgatgct | 60 |
| cagatttact tggaaaaacc agggtggcca cccatccaga caccagcgtc atggcctgcc | 120 |
| caaccccctg agaagcctgt tcaacccct cagaggcctg cccagccccc tcagtggcct | 180 |
| gcccagcccc ctcagtggcc tgcccagccc cctcagaggc tgcccagcc cctcagagg | 240 |
| cctgcccaaa cccagcagtg gcctggccaa ccccctcaga ggcctgccca gccccctcag | 300 |
| tggcctgccc aaccccctca gaggcctgcc caacccccct caaagacctgc ccaaccccct | 360 |
| cagaggcctc ccaaccccc tccgaggcct gcccaacccc ctcagtggcc tgttcatccc | 420 |
| cctcagtggc ctgtccaacc cggtacgccg cttcagaggc ctaaattccc ctctgaccca | 480 |
| ggctcaaagc agagctgtga tgttgatagc aacacaagg tgcagtgtgg acttcctgac | 540 |
| atcactgccg cccattgtga tgccattaac tgctgttttg atggacggat gtgcttctac | 600 |
| ggaaaagcag tgactgttca gtgtaccaag gatggccagt tgtggtggt ggtggccagg | 660 |
| gatgccactc tgcccagcct ggaactggac tccatcagcc tgctgggac aaacggaccc | 720 |
| cactgccatg ctattggcac aacttctgtc tttgccatct accagtttaa agtcactgaa | 780 |
| tgtggaactg tcatgacgga ggaaactgat actattatct atgagaatag gatgtcctct | 840 |
| tcatatcaag tggggggttgg ccccttggc tccatcacca gggacagcca atatgatcta | 900 |
| acattccagt gcagatataa gggcagtacc attgtggctg tggttattga tgtgaagccg | 960 |
| gttcctcctc caaatcctga tatagctcct ggacccctca cagttgagct cagactcggc | 1020 |

```
agcggaacat gccttaccaa gggatgtaat gaagaggaag tggcctacac ctcttactac    1080
acagaggcag actaccctgt caccaaggtc ctcagggatc ctgtgtacac tgaggttcgc    1140
atcctggcga ggacagatcc caacattgtg ctgaccctgg gtcgctgctg ggctaccaca    1200
aacccaaacc ctctcagcct gccccagtgg gaccttctca ttgatggatg tccttaccag    1260
gatgaccgtt acctgaccac tcccatcaat gtgggaccct cttcgggtct gtccttccca    1320
acccactaca ggcgcttcgt ccttaagatg ttcacctttg tggatccaat gtctatgacc    1380
cccctgaggg agacggtgtt catccattgt aatacagctg tgtgtctgcc atcccatgga    1440
gacagctgtg aaccaagatg ctacagaaag aggagagaca ttcctgctgc agtccagaag    1500
accaccagaa tcaagtctaa tttggtttcc agtggcgaac tgatcctgac tgacccaagg    1560
gagctcacca actag                                                    1575
```

<210> SEQ ID NO 15
<211> LENGTH: 1317
<212> TYPE: DNA
<213> ORGANISM: Oncorhynchus masou

<400> SEQUENCE: 15

```
atggcgatga agtggagtgt agtttgtctc gtggcagtgg ccatgcttgg ctgtctgtgt      60
gttgctcaga tttggccacc ctccattaaa ccagtgcagc aacccttcag acccaatcgt     120
ccaccacctc agcagcctca gcaaccaccg tatcagaaac ccaggatccc ccaaaagac     180 caaacccagg ccaagcagaa gtttgagaca ccattggatt ggacctatcc tctggaccca     240
aagccagagc ccaagattat tgggggctca gaggcgagaa ccctgtggc tgccaattca     300 gtgagggctg agtgcaggga gaacatggtc cacgtggaag cgaagcatga cctgctgggg     360
atcggccagt tgatccagct agaagacctc actttgggag actgcccctat gtctggattc     420 gacaatatca accaggtgct catctttgag tctccgctgc agtcatgtgg cagccagcta     480
aggatgacta ccaactccct catctacatc ttcactctat attacaaacc caaacctctg     540
gcaaacaccc ccctcatcag gacaaatgac gcgatgatca atattgagtg ccactatcca     600
aggaaacaca atgtgagcag cctggccctg atcccaacct ggaccccttt ctccgctgct     660
aagtatgcag aggaactcct gtacttctcc atgaggctca tgactgctga ctggcagtat     720
gagagggccg gtaacatgta cgtgtttggt gatatggtga acatcgaggc ctctgtcatg     780
cagtacttcc acgttcccct gcgtatcttt gtggacagct gtgtggccac cctggaaccc     840
aacataaacg ccaatcccag atatgccttc attgagaatc atgggtgtct gatcgatgcc     900 aaaaatgacag gttcccactc ccagttcatg cctcgttccg cagactacaa gctgtatttc     960
caggtggagg ctttcaggtt ccagagccag agggggagtg acccaattat tccgcagaaa    1020
acaaagatac cttttcagcc tgcggcagat tatcccgcta cgctcgacat gatcttcctt    1080
acctgtcacc tgaaggcaac cacaatcgct tccccattg attttgagta caaggcctgc    1140
tctttcatta atacgtggag ggaggctggt gggaatgatg agtgtgtgg ctgctgtgac    1200 tccacctgta gcaacaggaa gggacgcgat accactacac atcaaaaacc agcaaatata    1260
tgggagggag atgttcagct tggtcccatc tttatctcgg aaaaggttga gcaataa       1317
```

<210> SEQ ID NO 16
<211> LENGTH: 1405
<212> TYPE: DNA
<213> ORGANISM: Salmo salar

<400> SEQUENCE: 16

```
gaagtggtct taccaactcc ctcagaagct tgcccaaccc cttcctcaga agcctgccca      60
acctcttcct cagtggcctg tccaacccct tcctcagagg cctgctgaac cccttcctca     120
gaggcctgct caaccccttc ctcagtggcc tgtccaaccc cttcctcaga ggcctgctga     180
accccttcct cagaggcctg ctcaaccctt cctcagagg cctgtccaac cccttcctca      240
gagacctgct caacccttc ttcgaagcc tgcccaaccc atcctcaac ggatacccta       300
caccaaagac gacacaaaac agacctgtga ggttgtggac aaggacaagg tgtcgtgtgg     360
actttctggc atcactgctg cccaatgcca ggccatcagc tgctgttttg atggacggat     420
gtgcttctac gggaaaacag tgactttcca gtgtaccaag gatggccagt ttgtggtggt     480
ggtttccagg gatgccactc tgcccaacct tgagctagat ccatcagcc tgctagggc      540
aaacggagcc cactgcaccc ctgtcggcac cacatctgcc tttgccatct accagttcaa     600
agttactgaa tgtggaactg tggtgacgga ggaacctgat actattgtct atgagaacag     660
gatgtcctct tcatatgtag tggggattgg acccttcggc gacattacca gggacagcca     720
ctatgacctg gtcttccagt gtcggtatac tgggacttcc gttgagacat tggttatcga     780
ggtgaaaacg tatccaaaacc caacccagt ggtcactgtt gatgcagttc tcaacgtgga     840
gctccgactg gccaatggac gttgtctctc aagggatgt gatgaaatgc aagaagcata     900
cacctcttac tacacggtgg cagactaccc tgtcaccaag gtcctcaggg atcccgtgta     960
cgctgaggtt cgcatcctgg ggatgacaga tcccaatgtt gtcctgacac tggagcagtg    1020
ctgggccacc acagaccccca caggtgatag gctgccccgg tgggacctac tagttaatgg    1080
gtgtccctac caggatgacc gttacctgac cgtgcccatc gcctcggaca gctcctatat    1140
ccctccggga gaattcttat cccactacaa gcgcttcgtc ttcaagatgt tcacctttgt    1200
ggatccgaca tctatggtcc ccctgcagga gaacgtgtac atccactgtc gtgcaacagt    1260
gtgccacgct ctagcaggat cctgtgaaca aaggtgcaac aggcaaagga gagatctttc    1320
tgctcaaggc caaagaagaa ctaaaggaga tgttgtggtt ccagtcaaa aagtcatcat    1380
gattgaccca agtctttatg cttaa                                         1405
```

<210> SEQ ID NO 17
<211> LENGTH: 10
<212> TYPE: PRT
<213> ORGANISM: Salmo salar

<400> SEQUENCE: 17

Asp Gly Gln Phe Val Val Val Ser Arg
1               5                   10

<210> SEQ ID NO 18
<211> LENGTH: 11
<212> TYPE: PRT
<213> ORGANISM: Salmo salar

<400> SEQUENCE: 18

Asp Ser His Tyr Asp Leu Val Phe Gln Cys Arg
1               5                   10

<210> SEQ ID NO 19
<211> LENGTH: 14
<212> TYPE: PRT
<213> ORGANISM: Salmo salar

<400> SEQUENCE: 19

```
Tyr Thr Gly Thr Ser Val Glu Thr Leu Val Ile Glu Val Lys
1               5                   10

<210> SEQ ID NO 20
<211> LENGTH: 17
<212> TYPE: PRT
<213> ORGANISM: Salmo salar

<400> SEQUENCE: 20

Met Ser Ser Ser Tyr Val Val Gly Ile Gly Pro Phe Gly Asp Ile Thr
1               5                   10                  15

Arg

<210> SEQ ID NO 21
<211> LENGTH: 17
<212> TYPE: PRT
<213> ORGANISM: Salmo salar

<400> SEQUENCE: 21

Met Ser Ser Ser Tyr Val Val Gly Ile Gly Pro Phe Gly Asp Ile Thr
1               5                   10                  15

Arg

<210> SEQ ID NO 22
<211> LENGTH: 18
<212> TYPE: PRT
<213> ORGANISM: Salmo salar

<400> SEQUENCE: 22

Thr Val Thr Val Gln Cys Thr Lys Asp Gly Gln Phe Val Val Val Val
1               5                   10                  15

Ser Arg

<210> SEQ ID NO 23
<211> LENGTH: 20
<212> TYPE: PRT
<213> ORGANISM: Salmo salar

<400> SEQUENCE: 23

Val Thr Glu Cys Gly Thr Val Thr Glu Glu Pro Asp Thr Ile Val
1               5                   10                  15

Tyr Glu Asn Arg
            20

<210> SEQ ID NO 24
<211> LENGTH: 10
<212> TYPE: PRT
<213> ORGANISM: Salmo salar

<400> SEQUENCE: 24

Asp Gly Gln Phe Val Val Val Val Ala Arg
1               5                   10

<210> SEQ ID NO 25
<211> LENGTH: 11
<212> TYPE: PRT
<213> ORGANISM: Salmo salar

<400> SEQUENCE: 25

Thr Asp Pro Asn Ile Val Leu Thr Leu Gly Arg
1               5                   10
```

```
<210> SEQ ID NO 26
<211> LENGTH: 11
<212> TYPE: PRT
<213> ORGANISM: Salmo salar

<400> SEQUENCE: 26

Val Leu Arg Asp Pro Val Tyr Thr Glu Val Arg
1               5                   10

<210> SEQ ID NO 27
<211> LENGTH: 11
<212> TYPE: PRT
<213> ORGANISM: Salmo salar

<400> SEQUENCE: 27

Asp Ser Gln Tyr Asp Leu Thr Phe Gln Cys Arg
1               5                   10

<210> SEQ ID NO 28
<211> LENGTH: 14
<212> TYPE: PRT
<213> ORGANISM: Salmo salar

<400> SEQUENCE: 28

Met Phe Thr Phe Val Asp Pro Met Ser Met Thr Pro Leu Arg
1               5                   10

<210> SEQ ID NO 29
<211> LENGTH: 14
<212> TYPE: PRT
<213> ORGANISM: Salmo salar

<400> SEQUENCE: 29

Met Phe Thr Phe Val Asp Pro Met Ser Met Thr Pro Leu Arg
1               5                   10

<210> SEQ ID NO 30
<211> LENGTH: 14
<212> TYPE: PRT
<213> ORGANISM: Salmo salar

<400> SEQUENCE: 30

Met Phe Thr Phe Val Asp Pro Met Ser Met Thr Pro Leu Arg
1               5                   10

<210> SEQ ID NO 31
<211> LENGTH: 17
<212> TYPE: PRT
<213> ORGANISM: Salmo salar

<400> SEQUENCE: 31

Met Ser Ser Ser Tyr Gln Val Gly Val Gly Pro Phe Gly Ser Ile Thr
1               5                   10                  15

Arg

<210> SEQ ID NO 32
<211> LENGTH: 17
<212> TYPE: PRT
<213> ORGANISM: Salmo salar

<400> SEQUENCE: 32

Met Ser Ser Ser Tyr Gln Val Gly Val Gly Pro Phe Gly Ser Ile Thr
1               5                   10                  15

Arg
```

<210> SEQ ID NO 33
<211> LENGTH: 18
<212> TYPE: PRT
<213> ORGANISM: Salmo salar

<400> SEQUENCE: 33

Ala Val Thr Val Gln Cys Thr Lys Asp Gly Gln Phe Val Val Val
1               5                   10                  15

Ala Arg

<210> SEQ ID NO 34
<211> LENGTH: 20
<212> TYPE: PRT
<213> ORGANISM: Salmo salar

<400> SEQUENCE: 34

Val Thr Glu Cys Gly Thr Val Met Thr Glu Glu Thr Asp Thr Ile Ile
1               5                   10                  15

Tyr Glu Asn Arg
            20

<210> SEQ ID NO 35
<211> LENGTH: 20
<212> TYPE: PRT
<213> ORGANISM: Salmo salar

<400> SEQUENCE: 35

Val Thr Glu Cys Gly Thr Val Met Thr Glu Glu Thr Asp Thr Ile Ile
1               5                   10                  15

Tyr Glu Asn Arg
            20

<210> SEQ ID NO 36
<211> LENGTH: 13
<212> TYPE: PRT
<213> ORGANISM: Salmo salar

<400> SEQUENCE: 36

Ala Glu Cys Arg Glu Asn Met Val His Val Glu Ala Lys
1               5                   10

<210> SEQ ID NO 37
<211> LENGTH: 13
<212> TYPE: PRT
<213> ORGANISM: Salmo salar

<400> SEQUENCE: 37

Ala Glu Cys Arg Glu Asn Met Val His Val Glu Ala Lys
1               5                   10

<210> SEQ ID NO 38
<211> LENGTH: 14
<212> TYPE: PRT
<213> ORGANISM: Salmo salar

<400> SEQUENCE: 38

Thr Asn Asp Ala Met Ile Asn Ile Glu Cys His Tyr Pro Arg
1               5                   10

<210> SEQ ID NO 39
<211> LENGTH: 14
<212> TYPE: PRT

<213> ORGANISM: Salmo salar

<400> SEQUENCE: 39

Thr Asn Asp Ala Met Ile Asn Ile Glu Cys His Tyr Pro Arg
1               5                   10

<210> SEQ ID NO 40
<211> LENGTH: 11
<212> TYPE: PRT
<213> ORGANISM: Salmo salar

<400> SEQUENCE: 40

Tyr Ala Glu Glu Leu Leu Tyr Phe Ser Met Arg
1               5                   10

<210> SEQ ID NO 41
<211> LENGTH: 11
<212> TYPE: PRT
<213> ORGANISM: Salmo salar

<400> SEQUENCE: 41

Tyr Ala Glu Glu Leu Leu Tyr Phe Ser Met Arg
1               5                   10

<210> SEQ ID NO 42
<211> LENGTH: 10
<212> TYPE: PRT
<213> ORGANISM: Salmo salar

<400> SEQUENCE: 42

Leu Met Thr Ala Asp Trp Gln Tyr Glu Arg
1               5                   10

<210> SEQ ID NO 43
<211> LENGTH: 10
<212> TYPE: PRT
<213> ORGANISM: Salmo salar

<400> SEQUENCE: 43

Leu Met Thr Ala Asp Trp Gln Tyr Glu Arg
1               5                   10

<210> SEQ ID NO 44
<211> LENGTH: 19
<212> TYPE: PRT
<213> ORGANISM: Salmo salar

<400> SEQUENCE: 44

Ile Phe Val Asp Ser Cys Val Ala Thr Leu Glu Pro Asn Ile Asn Ala
1               5                   10                  15

Asn Pro Arg

<210> SEQ ID NO 45
<211> LENGTH: 11
<212> TYPE: PRT
<213> ORGANISM: Salmo salar

<400> SEQUENCE: 45

Met Thr Gly Ser His Ser Gln Phe Met Pro Arg
1               5                   10

<210> SEQ ID NO 46
<211> LENGTH: 9
<212> TYPE: PRT

```
<213> ORGANISM: Salmo salar

<400> SEQUENCE: 46

Leu Tyr Phe Gln Val Glu Ala Phe Arg
1               5
```